(12) United States Patent
Oshima et al.

(10) Patent No.: US 7,122,691 B2
(45) Date of Patent: Oct. 17, 2006

(54) PROCESS FOR PRODUCING COMPOUND, CATALYST COMPONENT FOR ADDITION POLYMERIZATION, PROCESS FOR PRODUCING CATALYST FOR ADDITION POLYMERIZATION, AND PROCESS FOR PRODUCING ADDITION POLYMER

(75) Inventors: Hideki Oshima, Ichihara (JP); Makoto Satoh, Ichihara (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 71 days.

(21) Appl. No.: 11/041,954

(22) Filed: Jan. 26, 2005

(65) Prior Publication Data

US 2005/0222351 A1    Oct. 6, 2005

(30) Foreign Application Priority Data

| Mar. 30, 2004 | (JP) | ............................. 2004-098494 |
| Mar. 30, 2004 | (JP) | ............................. 2004-098495 |
| Mar. 30, 2004 | (JP) | ............................. 2004-098496 |

(51) Int. Cl.
  C07F 5/06    (2006.01)
  B01J 31/00    (2006.01)
  C08F 4/44    (2006.01)
  C07F 17/00    (2006.01)

(52) U.S. Cl. ........................ 556/187; 556/1; 556/181; 556/182; 502/103; 502/117; 526/90; 526/108; 526/943

(58) Field of Classification Search .................... 556/1, 556/181, 182, 187; 502/103, 117; 526/90, 526/108, 943
See application file for complete search history

(56) References Cited

U.S. PATENT DOCUMENTS

| 4,276,399 A | | 6/1981 | Rekers et al. |
| 4,542,199 A | | 9/1985 | Kaminsky et al. |
| 4,732,993 A | * | 3/1988 | Malpass et al. ............. 556/181 |
| 4,990,640 A | | 2/1991 | Tsutsui et al. |
| 6,153,550 A | * | 11/2000 | Kissin ........................ 502/103 |
| 6,333,388 B1 | | 12/2001 | Kumamoto et al. |

FOREIGN PATENT DOCUMENTS

| EP | 0 277 004 A1 | 8/1988 |
| EP | 0 571 987 A2 | 12/1993 |
| JP | 10-17617 | 1/1998 |
| JP | 11-12319 | 1/1999 |
| JP | 11-343306 | 12/1999 |
| JP | 3196419 | 6/2001 |
| JP | 3264338 | 12/2001 |

* cited by examiner

Primary Examiner—Porfirio Nazario-Gonzalez
(74) Attorney, Agent, or Firm—Foley and Lardner LLP

(57) ABSTRACT

There are provided (1) a process for producing a compound, which comprises the step of contacting a compound (A) defined by the formula, $M^1L^1{}_3$, a compound (B) defined by the formula, $R^1{}_{t-1}TH$, and a compound (C) defined by the formula, $R^2{}_{t-2}TH_2$; (2) a catalyst component for addition polymerization, which comprises a compound produced by said process; (3) a process for producing a polymerization catalyst, which comprises the step of contacting said catalyst component with a transition metal compound and an optional organoaluminum compound; and (4) a process for producing an addition polymer, which comprises the step of addition polymerizing an addition polymerizable monomer in the presence of a catalyst produced by said process.

22 Claims, No Drawings

PROCESS FOR PRODUCING COMPOUND, CATALYST COMPONENT FOR ADDITION POLYMERIZATION, PROCESS FOR PRODUCING CATALYST FOR ADDITION POLYMERIZATION, AND PROCESS FOR PRODUCING ADDITION POLYMER

FIELD OF THE INVENTION

The present invention relates to a process for producing a compound suitable for a catalyst component of a catalyst for addition polymerization; a catalyst component for addition polymerization comprising said compound; a process for producing a catalyst for addition polymerization; and a process for producing an addition polymer.

BACKGROUND OF THE INVENTION

There are known the following so-called single-site catalysts, which polymerize an addition-polymerizable monomer such as an olefin to produce an addition polymer:

(1) a catalyst obtained by combining bis(cyclopentadienyl)zirconium dichloride with methylaluminoxane, and a catalyst obtained by combining said transition metal compound with a specific boron compound (JP 58-19309A, corresponding to U.S. Pat. No. 4,542,199);

(2) a catalyst obtained by combining bis(cyclopentadienyl)zirconium dimethyl with tri(n-butyl)ammonium tetraxis(pentafluorophenyl)borate (JP 1-502036W, corresponding to EP 277004A); and (3) a catalyst, which slightly lowers homogeneity of an addition polymer obtained (JP 5-320248A, corresponding to EP 571987A, JP 10-17617A, JP 11-12319A and JP 11-343306A), wherein the term "homogeneity" means uniformity of polymerization of a comonomer in case that said addition polymer is a copolymer.

SUMMARY OF THE INVENTION

However, each of the above-mentioned catalysts has a problem in that an addition polymer produced using a large amount of hydrogen as a molecular weight regulator has a small molecular weight.

In view of said problem, an object of the present invention is to provide (1) a process for producing an addition polymer, which has a large molecular weight even if produced using a large amount of hydrogen as a molecular weight regulator, (2) a process for producing a catalyst used for said process for producing an addition polymer; (3) a catalyst component used for said process for producing a catalyst, and (4) a process for producing a compound suitable for said catalyst component. This object is accomplished by an invention relating to a compound produced according to the "process-1" mentioned below.

Another object of the present invention is to provide (1) a process for producing a compound having a high performance using a cheap ethylaluminum compound as a starting material, (2) a catalyst component for addition polymerization comprising said compound, (3) a process for producing a catalyst for addition polymerization using said catalyst component for addition polymerization, and (4) a process for producing efficiently an addition polymer using a catalyst for addition polymerization produced by said process. This object is accomplished by an invention relating to a compound produced according to the "process-2" mentioned below.

Further, another object of the present invention is to provide (1) a process for producing a highly active catalyst for addition polymerization, (2) a catalyst component for addition polymerization used for said process, (3) a process for producing a compound used for said catalyst component for addition polymerization, and (4) a process for producing efficiently an addition polymer using a catalyst for addition polymerization produced by the process mentioned in the above (1). This object is accomplished by an invention relating to a compound produced according to the "process-3" mentioned below.

The present invention is a process for producing a compound, which comprises the step of contacting a compound (A) represented by the following formula [1], a compound (B) represented by the following formula [2], and a compound (C) represented by the following formula [3] with one another:

$$M^1 L^1_3 \qquad [1],$$

$$R^1_{t-1}TH \qquad [2] \text{ and}$$

$$R^2_{t-2}TH_2 \qquad [3],$$

in respective molar amounts satisfying the following formula (1), $$3\times(\text{molar amount of the compound (A)}) \leq (\text{molar amount of the compound (B)}) + 2\times(\text{molar amount of the compound (C)}) \qquad (1),$$

wherein $M^1$ is an atom of Group 13 in the periodic table; $L^1$ is a hydrogen atom, a hydrocarbon group or a halogen atom, three $L^1$s are the same as or different from one another, and at least one $L^1$ is a hydrocarbon group; $R^1$ is an electron-withdrawing group or a group containing an electron-withdrawing group, and when plural $R^1$s exist, they are the same as or different from one another; $R^2$ is a hydrocarbon group or a halogenated hydrocarbon group; T is independently of each other a non-metal atom of Group 15 or 16 in the periodic table; and t is the valence of T. This process is hereinafter referred to as "process-1".

Also, the present invention is a process for producing a compound, which comprises the step of contacting a compound (a) represented by the following formula [4], a compound (B) represented by the above-mentioned formula [2], and a compound (C) represented by the above-mentioned formula [3] with one another:

$$EtAlL^2_2 \qquad [4],$$

wherein $L^2$ is a hydrogen atom, a hydrocarbon group having two or more carbon atoms, or a halogen atom, and two $L^2$s are the same as or different from each another. This process is hereinafter referred to as "process-2".

Further, the present invention is a process for producing a compound, which comprises the step of contacting a compound (A) represented by the above-mentioned formula [1], a compound (b) represented by the following formula [5], and a compound (C) represented by the above-mentioned formula [3] with one another:

$$R^3 OH \qquad [5],$$

wherein $R^3$ is a halogenated alkyl group. This process is hereinafter referred to as "process-3".

The above-mentioned process-1, process-2 and process-3 are hereinafter collectively referred to as "processes of the present invention".

Still further, the present invention is a catalyst component (A) for addition polymerization, which comprises a compound produced according to each of the processes of the present invention.

Also, the present invention is a process for producing a catalyst for addition polymerization, which comprises the step of contacting the above-mentioned catalyst component (A) for addition polymerization, a transition metal compound (B) and an optional organoaluminum compound (C) with one another. The catalyst component (A) for addition polymerization, the transition metal compound (B) and the organoaluminum compound (C) are hereinafter referred to as "component (A)", "component (B)" and "component (C)", respectively.

Also, the present invention is a process for producing an addition polymer, which comprises the step of addition polymerizing an addition polymerizable monomer in the presence of a catalyst for addition polymerization produced according to the above-mentioned process.

DETAILED DESCRIPTION OF THE INVENTION

Examples of $M^1$ in the above formula [1] are a boron atom, an aluminum atom, a gallium atom, an indium atom and a thallium atom. Among them, a boron atom or an aluminum atom is preferable, and an aluminum atom is particularly preferable.

Examples of the halogen atom of $L^1$ in the above formula [1] are a fluorine atom, a chlorine atom, a bromine atom and an iodine atom.

The hydrocarbon group of $L^1$ in the above formula [1] is preferably an alkyl group, an aryl group or an aralkyl group.

Said alkyl group is preferably an alkyl group having 1 to 20 carbon atoms. Examples thereof are a methyl group, an ethyl group, a n-propyl group, an isopropyl group, a n-butyl group, a sec-butyl group, a tert-butyl group, an isobutyl group, a n-pentyl group, a neopentyl group, a n-hexyl group, a n-heptyl group, a n-octyl group, a n-decyl group, a n-dodecyl group, a n-pentadecyl group and a n-eicosyl group. More preferred is a methyl group, an ethyl group, an isopropyl group, a tert-butyl group or an isobutyl group.

One or more hydrogen atoms contained in the above-mentioned alkyl groups may be substituted with a halogen atom such as a fluorine atom, a chlorine atom, a bromine atom and an iodine atom. Examples of an alkyl group, whose one or more hydrogen atoms are substituted with a halogen atom, are a fluoromethyl group, a difluoromethyl group, a trifluoromethyl group, a fluoroethyl group, a difluoroethyl group, a trifluoroethyl group, a tetrafluoroethyl group, a pentafluoroethyl group, a perfluoropropyl group, a perfluorobutyl group, a perfluoropentyl group, a perfluorohexyl group, a perfluorooctyl group, a perfluorododecyl group, a perfluoropentadecyl group, a perfluoroeicosyl group, a 1H,1H-perfluoropropyl group, a 1H,1H-perfluorobutyl group, a 1H,1H-perfluoropentyl group, a 1H,1H-perfluorohexyl group, a 1H,1H-perfluorooctyl group, a 1H,1H-perfluorododecyl group, a 1H,1H-perfluoropentadecyl group and a 1H,1H-perfluoroeicosyl group; and alkyl groups obtained by changing the term "fluoro" contained in the above-mentioned alkyl groups to the term "chloro", "bromo" or "iodo".

The above-mentioned aryl group is preferably an aryl group having 6 to 20 carbon atoms. Examples thereof are a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, a n-propylphenyl group, an isopropylphenyl group, a n-butylphenyl group, a sec-butylphenyl group, a tert-butylphenyl group, an isobutylphenyl group, a n-pentylphenyl group, a neopentylphenyl group, a n-hexylphenyl group, a n-octylphenyl group, a n-decylphenyl group, a n-dodecylphenyl group, a n-tetradecylphenyl group, a naphthyl group and an anthracenyl group. Among them, more preferred is a phenyl group.

One or more hydrogen atoms contained in the above-mentioned aryl groups may be substituted with a halogen atom such as a fluorine atom, a chlorine atom, a bromine atom and an iodine atom; an alkoxy group such as a methoxy group and an ethoxy group; an aryloxy group such as a phenoxy group; or an aralkyloxy group such as a benzyloxy group.

The above-mentioned aralkyl group is preferably an aralkyl group having 7 to 20 carbon atoms. Examples thereof are a benzyl group, a (2-methylphenyl)methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl)methyl group, a (3,5-dimethylphenyl)methyl group, a (2,3,4-trimethylphenyl)methyl group, a (2,3,5-trimethylphenyl)methyl group, a (2,3,6-trimethylphenyl)methyl group, a (3,4,5-trimethylphenyl)methyl group, a (2,4,6-trimethylphenyl)methyl group, a (2,3,4,5-tetramethylphenyl)methyl group, a (2,3,4,6-tetramethylphenyl)methyl group, a (2,3,5,6-tetramethylphenyl)methyl group, a (pentamethylphenyl)methyl group, an (ethylphenyl)methyl group, a (n-propylphenyl)methyl group, an (isopropylphenyl)methyl group, a (n-butylphenyl)methyl group, a (sec-butylphenyl)methyl group, a (tert-butylphenyl)methyl group, an (isobutylphenyl)methyl group, a (n-pentylphenyl)methyl group, a (neopentylphenyl)methyl group, a (n-hexylphenyl)methyl group, a (n-octylphenyl)methyl group, a (n-decylphenyl)methyl group, a naphthylmethyl group and an anthracenylmethyl group. Among them, more preferred is a benzyl group.

One or more hydrogen atoms contained in the above-mentioned aralkyl groups may be substituted with a halogen atom such as a fluorine atom, a chlorine atom, a bromine atom and an iodine atom.

$L^1$ in the above formula [1] is preferably a hydrogen atom, an alkyl group, an aryl group or a halogen atom, further preferably a hydrogen atom, an alkyl group or a halogen atom, and particularly preferably an alkyl group.

T contained in the above formula [2] is the same as, or different from T contained in the above formula [3]. Examples of the non-metal atom of Group 15 of T in those formulas are a nitrogen atom and a phosphorous atom, and examples of the non-metal atom of the Group 16 of T therein are an oxygen atom and a sulfur atom. Among them, T is preferably a nitrogen atom or an oxygen atom, and particularly preferably an oxygen atom.

In the above formulas [2] and [3], when T is a non-metal atom of Group 15, t is 3, and when T is a non-metal atom of Group 16, t is 2.

As an index of an electron-withdrawing property of $R^1$ in the above formula [2], there is known a substituent constant σ in the Hammet's rule. Examples of the electron-withdrawing group are those having a positive substituent constant σ.

Examples of the electron-withdrawing group of $R^1$ in the above formula [2] are a fluorine atom, a chlorine atom, a bromine atom, an iodine atom, a cyano group, a nitro group, a carbonyl group, a sulfone group and a phenyl group. Examples of the group containing an electron-withdrawing group of $R^1$ in the above formula [2] are a halogenated alkyl group, a halogenated aryl group, a (halogenated alkyl)aryl group, a cyanated aryl group, a nitrated aryl group, an ester group (for example, an alkoxycarbonyl group, an aralkyloxycarbonyl group and an aryloxycarbonyl group), an acyl group and a halogenated acyl group.

Examples of the above-mentioned halogenated alkyl group of $R^1$ are a fluoromethyl group, a difluoromethyl group, a trifluoromethyl group, a 2,2,2-trifluoroethyl group, a 2,2,3,3,3-pentafluoropropyl group, a 2,2,2-trifluoro-1-trifluoromethylethyl group, a 1,1-bis(trifluoromethyl)-2,2,2-trifluoroethyl group, a 1H,1H-perfluorobutyl group, a 1H,1H-perfluoropentyl group, a 1H,1H-perfluorohexyl group, a 1H,1H-perfluorooctyl group, a 1H,1H-perfluorododecyl group, a 1H,1H-perfluoropentadecyl group and a 1H,1H-perfluoroeicosyl group; and halogenated alkyl groups obtained by changing the term "fluoro" contained in the above-mentioned halogenated alkyl groups to the term "chloro", "bromo" or "iodo".

Examples of the above-mentioned halogenated aryl group of $R^1$ are a 2-fluorophenyl group, a 3-fluorophenyl group, a 4-fluorophenyl group, a 2,4-difluorophenyl group, a 2,6-difluorophenyl group, a 3,4-difluorophenyl group, a 3,5-difluorophenyl group, a 2,4,6-trifluorophenyl group, a 3,4,5-trifluorophenyl group, a 2,3,5,6-tetrafluorophenyl group, a pentafluorophenyl group, a 2,3,5,6-tetrafluoro-4-trifluoromethylphenyl group, a 2,3,5,6-tetrafluoro-4-pentafluorophenylphenyl group, a perfluoro-1-naphtyl group, a perfluoro-2-naphtyl group and a 4,5,6,7,8-pentafluoro-2-naphtyl group; and halogenated aryl groups obtained by changing the term "fluoro" contained in the above-mentioned halogenated aryl groups to the term "chloro", "bromo" or "iodo".

Examples of the above-mentioned (halogenated alkyl)aryl group of $R^1$ are a 2-(trifluoromethyl)phenyl group, a 3-(trifluoromethyl)phenyl group, a 4-(trifluoromethyl)phenyl group, a 2,6-bis(trifluoromethyl)phenyl group, a 3,5-bis(trifluoromethyl)phenyl group, and a 2,4,6-tris(trifluoromethyl) phenyl group; and (halogenated alkyl)aryl groups obtained by changing the term "fluoro" contained in the above-mentioned (halogenated alkyl)aryl groups to the term "chloro", "bromo" or "iodo".

Examples of the above-mentioned cyanated aryl group of $R^1$ are a 2-cyanophenyl group, a 3-cyanophenyl group and a 4-cyanophenyl group.

Examples of the above-mentioned nitrated aryl group of $R^1$ are a 2-nitrophenyl group, a 3-nitrophenyl group and a 4-nitrophenyl group.

Examples of the above-mentioned ester group of $R^1$ are a methoxycarbonyl group, an ethoxycarbonyl group, a n-propoxycarbonyl group, an isopropoxycarbonyl group, a phenoxycarbonyl group, a trifluoromethoxycarbonyl group and a pentafluorophenoxycarbonyl group.

Examples of the above-mentioned acyl group of $R^1$ are a formyl group, an ethanoyl group, a propanoyl group, a butanoyl group, a trifluoroethanoyl group, a benzoyl group, a pentafluorobenzoyl group, a perfluoropentanoyl group, a perfluoropropanoyl group, a perfluorobutanoyl group, a perfluoropentanoyl group, a perfluorohexanoyl group, a perfluoroheptanoyl group, a perfluorooctanoyl group, a perfluorononanoyl group, a perfluorodecanoyl group, a perfluoroundecanoyl group and a perfluorododecanoyl group.

$R^1$ in the above formula [2] is preferably a halogenated hydrocarbon group; more preferably a halogenated alkyl group or a halogenated aryl group; further preferably a fluoromethyl group, a difluoromethyl group, a trifluoromethyl group, a 2,2,2-trifluoroethyl group, a 2,2,3,3,3-pentafluoropropyl group, a 2,2,2-trifluoro-1-trifluoromethylethyl group, a 1,1-bis(trifluoromethyl)-2,2,2-trifluoroethyl group, a 2-fluorophenyl group, a 3-fluorophenyl group, a 4-fluorophenyl group, a 2,4-difluorophenyl group, a 2,6-difluorophenyl group, a 3,4-difluorophenyl group, a 3,5-difluorophenyl group, a 2,4,6-trifluorophenyl group, a 3,4,5-trifluorophenyl group, a 2,3,5,6-tetrafluorophenyl group, a pentafluorophenyl group, a 2,3,5,6-tetrafluoro-4-trifluoromethylphenyl group, a 2,3,5,6-tetrafluoro-4-pentafluorophenylphenyl group, a perfluoro-1-naphtyl group, a perfluoro-2-naphtyl group, a 4,5,6,7,8-pentafluoro-2-naphtyl group, a chloromethyl group, a dichloromethyl group, a trichloromethyl group, a 2,2,2-trichloroethyl group, a 2,2,3,3,3-pentachloropropyl group, a 2,2,2-trichloro-1-trichloromethylethyl group, a 1,1-bis(trichloromethyl)-2,2,2-trichloroethyl group, a 4-chlorophenyl group, a 2,6-dichlorophenyl group, a 3,5-dichlorophenyl group, a 2,4,6-trichlorophenyl group, a 3,4,5-trichlorophenyl group or a pentachlorophenyl group; particularly preferably a fluoroalkyl group or a fluoroaryl group; and most preferably a trifluoromethyl group, a 2,2,2-trifluoro-1-trifluoromethylethyl group, a 1,1-bis(trifluoromethyl)-2,2,2-trifluoroethyl group, a 3,5-difluorophenyl group, a 3,4,5-trifluorophenyl group or a pentafluorophenyl group.

The hydrocarbon group of $R^2$ in the above formula [3] is preferably an alkyl group, an aryl group or an aralkyl group, and examples thereof are those exemplified for $L^1$ in the above formula [1].

Examples of the halogenated hydrocarbon group of $R^2$ in the above formula [3] are a halogenated alkyl group, a halogenated aryl group and a (halogenated alkyl)aryl group, and specific examples thereof are those exemplified for the electron-withdrawing group of $R^1$ in the above formula [2].

$R^2$ in the above formula [3] is preferably a halogenated hydrocarbon group, and further preferably a fluorinated hydrocarbon group.

Examples of the above-mentioned compound (A) having an aluminum atom as $M^1$ are a trialkylaluminum such as trimethylaluminum, triethylaluminum, tripropylaluminum, tri-n-butylaluminum, triisobutylaluminum, tri-n-hexylaluminum and tri-n-octylaluminum; a triarylaluminum such as triphenylaluminum, trinaphthylaluminum and tri(pentafluorophenyl)aluminum; a trialkenylaluminum such as triallylaluminum; tri(cyclopentadienyl)aluminum; a dialkylaluminum halide such as dimethylaluminum chloride, diethylaluminum chloride, dipropylaluminum chloride, di-n-butylaluminum chloride, diisobutylaluminum chloride, di-n-hexylaluminum chloride, di-n-octylaluminum chloride, dimethylaluminum bromide, diethylaluminum bromide, dipropylaluminum bromide, di-n-butylaluminum bromide, diisobutylaluminum bromide, di-n-hexylaluminum bromide, di-n-octylaluminum bromide, dimethylaluminum iodide, diethylaluminum iodide, dipropylaluminum iodide, di-n-butylaluminum iodide, diisobutylaluminum iodide, di-n-hexylaluminum iodide and di-n-octylaluminum iodide; and an alkylaluminum dihalide such as methylaluminum dichloride, ethylaluminum dichloride, propylaluminum dichloride, n-butylaluminum dichloride, isobutylaluminum dichloride, n-hexylaluminum dichloride, n-octylaluminum dichloride, methylaluminum dibromide, ethylaluminum dibromide, propylaluminum dibromide, n-butylaluminum dibromide, isobutylaluminum dibromide, n-hexylaluminum dibromide, n-octylaluminum dibromide, methylaluminum diiodide, ethylaluminum diiodide, propylaluminum diiodide, n-butylaluminum diiodide, isobutylaluminum diiodide, n-hexylaluminum diiodide and n-octylaluminum diiodide.

The compound (A) is preferably a trialkylaluminum, further preferably trimethylaluminum, triethylaluminum, tripropylaluminum, tri-n-butylaluminum, triisobutylaluminum, tri-n-hexylaluminum or tri-n-octylaluminum, and particularly preferably trimethylaluminum, triethylaluminum, triisobutylaluminum or tri-n-octylaluminum.

Examples of amines and phosphine compounds of the above-mentioned compound (B) are amines such as di(fluoromethyl)amine, di(chloromethyl)amine, di(bromomethyl)amine, di(iodomethyl)amine, bis(difluoromethyl)amine, bis(dichloromethyl)amine, bis(dibromomethyl)amine, bis(diiodomethyl)amine, bis(trifluoromethyl)amine, bis(trichloromethyl)amine, bis(tribromomethyl)amine, bis(triiodomethyl)amine, bis (2,2,2-trifluoroethyl)amine, bis(2,2,2-trichloroethyl)amine, bis(2,2,2-tribromoethyl)amine, bis(2,2,2-triiodoethyl)amine, bis(2,2,3,3,3-pentafluoropropyl)amine, bis(2,2,3,3,3-pentachloropropyl)amine, bis(2,2,3,3,3-pentabromopropyl)amine, bis(2,2,3,3,3-pentaiodopropyl)amine, bis(2,2,2-trifluoro-1-trifluoromethylethyl)amine, bis(2,2,2-trichloro-1-trichloromethylethyl)amine, bis(2,2,2-tribromo-1-tribromomethylethyl)amine, bis(2,2,2-triiodo-1-triiodomethylethyl)amine, bis(1,1-bis(trifluoromethyl)-2,2,2-trifluoroethyl)amine, bis(1,1-bis(trichloromethyl)-2,2,2-trichloroethyl)amine, bis(1,1-bis(tribromomethyl)-2,2,2-tribromoethyl)amine, bis(1,1-bis(triiodomethyl)-2,2,2-triiodoethyl)amine, bis(2-fluorophenyl)amine, bis(3-fluorophenyl)amine, bis(4-fluorophenyl)amine, bis(2-chlorophenyl)amine, bis(3-chlorophenyl)amine, bis(4-chlorophenyl)amine, bis(2-bromophenyl)amine, bis(3-bromophenyl)amine, bis(4-bromophenyl)amine, bis(2-iodophenyl)amine, bis(3-iodophenyl)amine, bis(4-iodophenyl)amine, bis(2,6-difluorophenyl)amine, bis(3,5-difluorophenyl)amine, bis(2,6-dichlorophenyl)amine, bis(3,5-dichlorophenyl)amine, bis(2,6-dibromophenyl)amine, bis(3,5-dibromophenyl)amine, bis(2,6-diiodophenyl)amine, bis(3,5-diiodophenyl)amine, bis(2,4,6-trifluorophenyl)amine, bis(2,4,6-trichlorophenyl)amine, bis(2,4,6-tribromophenyl)amine, bis(2,4,6-triiodophenyl)amine, bis(3,4,5-trifluorophenyl)amine, bis(3,4,5-trichlorophenyl)amine, bis(3,4,5-tribromophenyl)amine, bis(3,4,5-triiodophenyl)amine, bis(pentafluorophenyl)amine, bis(pentachlorophenyl)amine, bis(pentabromophenyl)amine, bis(pentaiodophenyl)amine, bis(2-(trifluoromethyl)phenyl)amine, bis(3-(trifluoromethyl)phenyl)amine, bis(4-(trifluoromethyl)phenyl)amine, bis(2,6-di(trifluoromethyl)phenyl)amine, bis(3,5-di(trifluoromethyl)phenyl)amine, bis(2,4,6-tri(trifluoromethyl)phenyl)amine, bis(2-cyanophenyl)amine, bis(3-cyanophenyl)amine, bis(4-cyanophenyl)amine, bis(2-nitrophenyl)amine, bis(3-nitrophenyl)amine, bis(4-nitrophenyl)amine, bis(1H,1H-perfluorobutyl)amine, bis(1H,1H-perfluoropentyl)amine, bis (1H,1H-perfluorohexyl)amine, bis (1H,1H-perfluorooctyl)amine, bis(1H,1H-perfluorododecyl)amine, bis(1H,1H-perfluoropentadecyl)amine, bis(1H,1H-perfluoroeicosyl)amine, bis(1H,1H-perchlorobutyl)amine, bis(1H,1H-perchloropentyl)amine, bis(1H,1H-perchlorohexyl)amine, bis (1H,1H-perchlorooctyl)amine, bis(1H,1H-perchlorododecyl)amine, bis(1H,1H-perchloropentadecyl)amine, bis(1H,1H-perchloroeicosyl)amine, bis(1H,1H-perbromobutyl)amine, bis(1H,1H-perbromopentyl)amine, bis(1H,1H-perbromohexyl)amine, bis(1H,1H-perbromooctyl)amine, bis(1H,1H-perbromododecyl)amine, bis(1H,1H-perbromopentadecyl)amine and bis(1H,1H-perbromoeicosyl)amine; and phosphine compounds obtained by changing the nitrogen atom contained in each of the above-mentioned amines to a phosphorus atom, each of which phosphine compounds has a name obtained by changing the term "amine" contained in each of the above-mentioned amines to the term "phosphine".

Examples of alcohols and thiol compounds of the above-mentioned compound (B) are alcohols such as fluoromethanol, chloromethanol, bromomethanol, iodomethanol, difluoromethanol, dichloromethanol, dibromomethanol, diiodomethanol, trifluoromethanol, trichloromethanol, tribromomethanol, triiodomethanol, 2,2,2-trifluoroethanol, 2,2,2-trichloroethanol, 2,2,2-tribromoethanol, 2,2,2-triiodoethanol, 1,1,1,3,3,3-hexafluoro-2-propanol, 1,1,1,3,3,3-hexachloro-2-propanol, 1,1,1,3,3,3-hexabromo-2-propanol, 1,1,1,3,3,3-hexaiodo-2-propanol, 1,1,1,3,3,3-hexafluoro-2-(trifluoromethyl)-2-propanol, 1,1,1,3,3,3-hexachloro-2-(trichloromethyl)-2-propanol, 1,1,1,3,3,3-hexabromo-2-(tribromomethyl)-2-propanol, 1,1,1,3,3,3-hexaiodo-2-(triiodomethyl)-2-propanol, 1H,1H,3H-perfluoropropanol, 1H,1H,3H-perchloropropanol, 1H,1H,3H-perbromopropanol, 1H,1H,3H-periodopropanol, 1H,1H-perfluoropropanol, 1H,1H-perchloropropanol, 1H,1H-perbromopropanol, 1H,1H-periodopropanol, 1H,1H,4H-perfluorobutanol, 1H,1H,4H-perchlorobutanol, 1H,1H,4H-perbromobutanol, 1H,1H,4H-periodobutanol, 1H,1H-perfluorobutanol, 1H,1H-perchlorobutanol, 1H,1H-perbromobutanol, 1H,1H-periodobutanol, 1H,1H,5H-perfluoropentanol, 1H,1H,5H-perchloropentanol, 1H,1H,5H-perbromopentanol, 1H,1H,5H-periodopentanol, 1H,1H-perfluoropentanol, 1H,1H-perchloropentanol, 1H,1H-perbromopentanol, 1H,1H-periodopentanol, 1H,1H,6H-perfluorohexanol, 1H,1H,6H-perchlorohexanol, 1H,1H,6H-perbromohexanol, 1H,1H,6H-periodohexanol, 1H,1H-perfluorohexanol, 1H,1H-perchlorohexanol, 1H,1H-perbromohexanol, 1H,1H-periodohexanol, 1H,1H,8H-perfluorooctanol, 1H,1H,8H-perchlorooctanol, 1H,1H,8H-perbromooctanol, 1H,1H,8H-periodooctanol, 1H,1H-perfluorooctanol, 1H,1H-perchlorooctanol, 1H,1H-perbromooctanol and 1H,1H-periodooctanol; and thiol compounds obtained by changing the oxygen atom contained in each of the above-mentioned alcohols to a sulfur atom, each of which thiol compounds has a name obtained by changing the term "ol" contained in each of the above-mentioned alcohols to the term "thiol".

Examples of phenols, naphthols, thiophenols and naphthylthiols of the above-mentioned compound (B) are phenols and naphthols such as 2-fluorophenol, 3-fluorophenol, 4-fluorophenol, 2,4-difluorophenol, 2,6-difluorophenol, 3,4-difluorophenol, 3,5-difluorophenol, 2,4,6-trifluorophenol, 3,4,5-trifluorophenol, 2,3,5,6-tetrafluorophenol, pentafluorophenol, 2,3,5,6-tetrafluoro-4-trifluoromethylphenol, 2,3,5,6-tetrafluoro-4-pentafluorophenylphenol, perfluoro-1-naphthol, perfluoro-2-naphthol, 4,5,6,7,8-pentafluoro-2-naphthol, 2-chlorophenol, 3-chlorophenol, 4-chlorophenol, 2,4-dichlorophenol, 2,6-dichlorophenol, 3,4-dichlorophenol, 3,5-dichlorophenol, 2,4,6-trichlorophenol, 3,4,5-trichlorophenol, 2,3,5,6-tetrachlorophenol, pentachlorophenol, 2,3,5,6-tetrachloro-4-trichloromethylphenol, 2,3,5,6-tetrachloro-4-pentachlorophenylphenol, perchloro-1-naphthol, perchloro-2-naphthol, 4,5,6,7,8-pentachloro-2-naphthol, 2-bromophenol, 3-bromophenol, 4-bromophenol, 2,4-dibromophenol, 2,6-dibromophenol, 3,4-dibromophenol, 3,5-dibromophenol, 2,4,6-tribromophenol, 3,4,5-tribromophenol, 2,3,5,6-tetrabromophenol, pentabromophenol, 2,3,5,6-tetrabromo-4-tribromomethylphenol, 2,3,5,6-tetrabromo-4-pentabromophenylphenol, perbromo-1-naphthol, perbromo-2-naphthol, 4,5,6,7,8-pentabromo-2-naphthol, 2-iodophenol, 3-iodophenol, 4-iodophenol, 2,4-diiodophenol, 2,6-diiodophenol, 3,4-diiodophenol, 3,5-diiodophenol, 2,4,6-triiodophenol, 3,4,5-triiodophenol, 2,3,5,6-tetraiodophenol, pentaiodophenol, 2,3,5,6-tetraiodo-4-triiodomethylphenol, 2,3,5,6-tetraiodo-4-pentaiodophenylphenol, periodo-1-naphthol, periodo-2-naphthol, 4,5,6,7,8-pentaiodo-2-naphthol, 2-(trifluoromethyl)phenol, 3-(trifluoromethyl)phenol, 4-(trifluoromethyl)phenol, 2,6-bis(trifluoromethyl)phenol, 3,5-bis(trifluoromethyl)phenol, 2,4,6-tris(trifluoromethyl)phenol, 2-cyanophenol, 3-cyanophenol, 4-cyanophenol, 2-nitrophenol, 3-nitrophenol and 4-nitrophenol; and thiophenols and naphthylthiols obtained by changing the oxygen atom contained in each of the above-mentioned phenols and naphthols to a sulfur atom, each of which thiophenols and naphthylthiols has a name obtained by changing the terms "phenol" and "naphthol" contained in each of the above-mentioned phenols and naphthols to the terms "thiophenol" and "naphthylthiol", respectively.

Examples of halogenated carboxylic acids of the above-mentioned compound (B) are pentafluorobenzoic acid, perfluoroethanoic acid, perfluoropropanoic acid, perfluorobutanoic acid, perfluoropentanoic acid, perfluorohexanoic acid, perfluoroheptanoic acid, perfluorooctanoic acid, perfluorononanoic acid, perfluorodecanoic acid, perfluoroundecanoic acid and perfluorododecanoic acid.

The compound (B) is preferably, as amines, bis(trifluoromethyl)amine, bis (2,2,2-trifluoroethyl)amine, bis(2,2,3,3-pentafluoropropyl)amine, bis(2,2,2-trifluoro-1-trifluoromethylethyl)amine, bis(1,1-bis(trifluoromethyl)-2,2,2-trifluoroethyl)amine or bis(pentafluorophenyl)amine; as alcohols, trifluoromethanol, 2,2,2-trifluoroethanol, 1,1,1,3,3,3-hexafluoro-2-propanol, 1,1,1,3,3,3-hexafluoro-2-(trifluoromethyl)-2-propanol, 1H,1H,6H-perfluorohexanol, 1H,1H-perfluorohexanol, 1H,1H,8H-perfluorooctanol or 1H,1H-perfluorooctanol; and as phenols, 2-fluorophenol, 3-fluorophenol, 4-fluorophenol, 2,6-difluorophenol, 3,5-difluorophenol, 2,4,6-trifluorophenol, 3,4,5-trifluorophenol, pentafluorophenol, 2-(trifluoromethyl)phenol, 3-(trifluoromethyl)phenol, 4-(trifluoromethyl)phenol, 2,6-bis(trifluoromethyl)phenol, 3,5-bis(trifluoromethyl)phenol or 2,4,6-tris(trifluoromethyl)phenol.

The compound (B) is more preferably bis(trifluoromethyl)amine, bis(pentafluorophenyl)amine, trifluoromethanol, 1,1,1,3,3,3-hexafluoro-2-propanol, 1,1,1,3,3,3-hexafluoro-2-(trifluoromethyl)-2-propanol, 2,6-difluorophenol, 3,5-difluorophenol, 2,4,6-trifluorophenol, 3,4,5-trifluorophenol, pentafluorophenol, 4-(trifluoromethyl)phenol, 2,6-bis(trifluoromethyl)phenol or 2,4,6-tris(trifluoromethyl)phenol; and further preferably 1,1,1,3,3,3-hexafluoro-2-propanol, 1,1,1,3,3,3-hexafluoro-2-(trifluoromethyl)-2-propanol, 3,5-difluorophenol, 3,4,5-trifluorophenol or pentafluorophenol.

Examples of the above-mentioned compound (C) are water, hydrogen sulfide, an alkylamine, an arylamine, an aralkylamine, a halogenated alkylamine, a halogenated arylamine and a (halogenated alkyl)arylamine. Examples of the alkylamine, the arylamine, the aralkylamine, the halogenated alkylamine, the halogenated arylamine and the (halogenated alkyl)arylamine are methylamine, ethylamine, n-propylamine, isopropylamine, n-butylamine, sec-butylamine, tert-butylamine, isobutylamine, n-pentylamine, neopentylamine, isopentylamine, n-hexylamine, n-octylamine, n-decylamine, n-dodecylamine, n-pentadecylamine, n-eicosylamine, alkylamine, cyclopentadienylamine, aniline, 2-tolylamine, 3-tolylamine, 4-tolylamine, 2,3-xylylamine, 2,4-xylylamine, 2,5-xylylamine, 2,6-xylylamine, 3,4-xylylamine, 3,5-xylylamine, 2,3,4-trimethylaniline, 2,3,5-trimethylaniline, 2,3,6-trimethylaniline, 2,4,6-trimethylaniline, 3,4,5-trimethylaniline, 2,3,4,5-tetramethylaniline, 2,3,4,6-tetramethylaniline, 2,3,5,6-tetramethylaniline, pentamethylaniline, ethylaniline, n-propylaniline, isopropylaniline, n-butylaniline, sec-butylaniline, tert-butylaniline, n-pentylaniline, neopentylaniline, n-hexylaniline, n-octylaniline, n-decylaniline, n-dodecylaniline, n-tetradecylaniline, naphthylamine, anthracenylamine, benzylamine, (2-methylphenyl)methylamine, (3-methylphenyl)methylamine, (4-methylphenyl)methylamine, (2,3-dimethylphenyl)methylamine, (2,4-dimethylphenyl)methylamine, (2,5-dimethylphenyl)methylamine, (2,6-dimethylphenyl)methylamine, (3,4-dimethylphenyl)methylamine, (3,5-dimethylphenyl)methylamine, (2,3,4-trimethylphenyl)methylamine, (2,3,5-trimethylphenyl)methylamine, (2,3,6-trimethylphenyl)methylamine, (3,4,5-trimethylphenyl)methylamine, (2,4,6-trimethylphenyl)methylamine, (2,3,4,5-tetramethylphenyl)methylamine, (2,3,4,6-tetramethylphenyl)methylamine, (2,3,5,6-tetramethylphenyl)methylamine, (pentamethylphenyl)methylamine, (ethylphenyl)methylamine, (n-propylphenyl)methylamine, (isopropylphenyl)methylamine, (n-butylphenyl)methylamine, (sec-butylphenyl)methylamine, (tert-butylphenyl)methylamine, (n-pentylphenyl)methylamine, (neopentylphenyl)methylamine, (n-hexylphenyl)methylamine, (n-octylphenyl)methylamine, (n-decylphenyl)methylamine, (n-tetradecylphenyl)methylamine, naphtylmethylamine, anthracenylmethylamine, fluoromethylamine, chloromethylamine, bromomethylamine, iodomethylamine, difluoromethylamine, dichloromethylamine, dibromomethylamine, diiodomethylamine, trifluoromethylamine, trichloromethylamine, tribromomethylamine, triiodomethylamine, 2,2,2-trifluoroethylamine, 2,2,2-trichloroethylamine, 2,2,2-tribromoethylamine, 2,2,2-triiodoethylamine, 2,2,3,3,3-pentafluoropropylamine, 2,2,3,3,3-pentachloropropylamine, 2,2,3,3,3-pentabromopropylamine, 2,2,3,3,3-pentaiodopropylamine, 2,2,2-trifluoro-1-trifluoromethylethylamine, 2,2,2-trichloro-1-trichloromethylethylamine, 2,2,2-tribromo-1-tribromomethylethylamine, 2,2,2-triiodo-1-triiodomethylethylamine, 1,1-bis(trifluoromethyl)-2,2,2-trifluoroethylamine, 1,1-bis(trichloromethyl)-2,2,2-trichloroethylamine, 1,1-bis(tribromomethyl)-2,2,2-tribromoethylamine, 1,1-bis(triiodomethyl)-2,2,2-triiodoethylamine, perfluoropropylamine, perchloropropylamine, perbromopropylamine, periodopropylamine, perfluorobutylamine, perchlorobutylamine, perbromobutylamine, periodobutylamine, perfluoropentylamine, perchloropentylamine, perbromopentylamine, periodopentylamine, perfluorohexylamine, perchlorohexylamine, perbromohexylamine, periodohexylamine, perfluorooctylamine, perchlorooctylamine, perbromooctylamine, periodooctylamine, perfluorododecylamine, perchlorododecylamine, perbromododecylamine, periodododecylamine, perfluoropentadecylamine, perchloropentadecylamine, perbromopentadecylamine, periodopentadecylamine, perfluoroeicosylamine, perchloroeicosylamine, perbromoeicosylamine, periodoeicosylamine, 2-fluoroaniline, 3-fluoroaniline, 4-fluoroaniline, 2-chloroaniline, 3-chloroaniline, 4-chloroaniline, 2-bromoaniline, 3-bromoaniline, 4-bromoaniline, 2-iodoaniline, 3-iodoaniline, 4-iodoaniline, 2,6-difluoroaniline, 3,5-difluoroaniline, 2,6-dichloroaniline, 3,5-dichloroaniline, 2,6-dibromoaniline, 3,5-dibromoaniline, 2,6-diiodoaniline, 3,5-diiodoaniline, 2,4,6-trifluoroaniline, 2,4,6-trichloroaniline, 2,4,6-tribromoaniline, 2,4,6- triiodoaniline, 3,4,5-trifluoroaniline, 3,4,5-trichloroaniline, 3,4,5-tribromoaniline, 3,4,5-triiodoaniline, pentafluoroaniline, pentachloroaniline, pentabromoaniline, pentaiodoaniline, 2-(trifluoromethyl)aniline, 3-(trifluoromethyl)aniline, 4-(trifluoromethyl)aniline, 2,6-di(trifluoromethyl)aniline, 3,5-di(trifluoromethyl)aniline and 2,4,6-tri(trifluoromethyl) aniline.

The compound (C) is preferably water, hydrogen sulfide, methylamine, ethylamine, n-propylamine, isopropylamine, n-butylamine, sec-butylamine, tert-butylamine, isobutylamine, n-octylamine, aniline, 2,6-xylylamine, 2,4,6-trimethylaniline, naphthylamine, anthracenylamine, benzylamine, trifluoromethylamine, pentafluoroethylamine, perfluoroproylamine, perfluorobutylamine, perfluoropentylamine, perfluorohexylamine, perfluorooctylamine, perfluorododecylamine, perfluoropentadecylamine, perfluoroeicosylamine, 2-fluoroaniline, 3-fluoroaniline, 4-fluoroaniline, 2,6-difluoroaniline, 3,5-difluoroaniline, 2,4,6-trifluoroaniline, 3,4,5-trifluoroaniline, pentafluoroaniline, 2-(trifluoromethyl)aniline, 3-(trifluoromethyl)aniline, 4-(trifluoromethyl)aniline, 2,6-bis(trifluoromethyl)aniline, 3,5-bis (trifluoromethyl)aniline or 2,4,6-tris(trifluoromethyl)aniline; particularly preferably water, trifluoromethylamine, perfluorobutylamine, perfluorooctylamine, perfluoropentadecylamine, 2-fluoroaniline, 3-fluoroaniline, 4-fluoroaniline, 2,6-difluoroaniline, 3,5-difluoroaniline, 2,4,6-trifluoroaniline, 3,4,5-trifluoroaniline, pentafluoroaniline, 2-(trifluoromethyl)aniline, 3-(trifluoromethyl)aniline, 4-(trifluoromethyl) aniline, 2,6-bis(trifluoromethyl)aniline, 3,5-bis(trifluoromethyl)aniline or 2,4,6-tris(trifluoromethyl)aniline; and most preferably water or pentafluoroaniline.

The compound (a) represented by the above formula [4] is a compound contained in the compound (A) represented by the above formula [1].

Examples of the halogen atom of $L^2$ in the formula [4] are the same as those of the halogen atom of $L^1$ mentioned above.

Examples of the hydrocarbon group of $L^2$ are the same as those of the hydrocarbon group of $L^1$ mentioned above, wherein a hydrocarbon group having one carbon atom is excluded.

$L^2$ is preferably a hydrogen atom, an alkyl group, an aryl group or a halogen atom; further preferably a hydrogen atom, an alkyl group or a halogen atom; particularly preferably an alkyl group; and most preferably an ethyl group.

Examples of the compound (a) are triethylaluminum; an ethyldialkylaluminum such as ethyldi-n-propylaluminum, ethyldiisopropylaluminum, di-n-butylethylaluminum, diisobutylethylaluminum, ethyldi-n-hexylaluminum and ethyldi-n-octylaluminum; an diethylalkylaluminum such as diethyl-n-propylaluminum, diethylisopropylaluminum, n-butyldiethylaluminum, isobutyldiethylaluminum, diethyl-n-hexylaluminum and diethyl-n-octylaluminum; a dialkylaluminum halide such as diethylaluminum chloride, diethylaluminum bromide and diethylaluminum iodide; and an ethylaluminum dihalide such as ethylaluminum dichloride, ethylaluminum dibromide and ethylaluminum diiodide.

The compound (a) is preferably triethylaluminum, an ethyldialkylaluminum or an diethylalkylaluminum; and most preferably triethylaluminum.

The compound (b) represented by the above formula [5] is a compound contained in the compound (B) represented by the above formula [2].

Examples of the halogenated alkyl group of $R^3$ in the formula [5] are a fluoromethyl group, a difluoromethyl group, a trifluoromethyl group, a 2,2,2-trifluoroethyl group, a 2,2,3,3,3-pentafluoropropyl group, a 1,1-bis(trifluoromethyl)-2,2,2-trifluoroethyl group, a 1,1,1,3,3,3-hexafluoropropyl group, a perfluoro-n-butyl group, a perfluoroisobutyl group, a perfluoro-sec-butyl group, a 1H,1H-perfluorobutyl group, a 1H,1H-perfluoropentyl group, a 1H,1H-perfluorohexyl group, a 1H,1H-perfluorooctyl group, a 1H,1H-perfluorododecyl group, a 1H,1H-perfluoropentadecyl group and a 1H,1H-perfluoroeicosyl group; and halogenated alkyl groups obtained by changing the term "fluoro" contained in the above-mentioned halogenated alkyl groups to the term "chloro", "bromo" or "iodo".

$R^3$ is preferably a fluoromethyl group, a difluoromethyl group, a trifluoromethyl group, a 2,2,2-trifluoroethyl group, a 2,2,3,3,3-pentafluoropropyl group, a 1,1-bis(trifluoromethyl)-2,2,2-trifluoroethyl group, a 1,1,1,3,3,3-hexafluoropropyl group, a perfluoro-n-butyl group, a perfluoroisobutyl group or a perfluoro-sec-butyl group; and particularly preferably a trifluoromethyl group, a 2,2,2-trifluoroethyl group, a 2,2,3,3,3-pentafluoropropyl group, a 1,1-bis(trifluoromethyl)-2,2,2-trifluoroethyl group or a 1,1,1,3,3,3-hexafluoropropyl group.

Examples of the compound (b) are the above-mentioned alcohol compounds exemplified as the compound (B).

The compound (b) is preferably trifluoromethanol, 2,2,2-trifluoroethanol, 1,1,1,3,3,3-hexafluoro-2-propanol, 1,1,1,3,3,3-hexafluoro-2-(trifluoromethyl)-2-propanol, 1H,1H,6H-perfluorohexanol, 1H,1H-perfluorohexanol, 1H,1H,8H-perfluorooctanol or 1H,1H-perfluorooctanol; more preferably trifluoromethanol, 1,1,1,3,3,3-hexafluoro-2-propanol or 1,1,1,3,3,3-hexafluoro-2-(trifluoromethyl)-2-propanol; and further preferably 1,1,1,3,3,3-hexafluoro-2-propanol or 1,1,1,3,3,3-hexafluoro-2-(trifluoromethyl)-2-propanol.

In the process-1 in accordance with the present invention, a method for contacting the compounds (A), (B) and (C) is not particularly limited. Examples of the method are as follows:

(1) a method comprising the steps of (i) contacting the compounds (A) and (B) to produce a contact product, and then (ii) contacting the contact product with the compound (C);

(2) a method comprising the steps of (i) contacting the compounds (A) and (C) to produce a contact product, and then (ii) contacting the contact product with the compound (B); and (3) a method comprising the steps of (i) contacting the compounds (B) and (C) to produce a contact product, and then (ii) contacting the contact product with the compound (A).

Among those methods, preferred is the method (1) or (2). In the process-2 in accordance with the present invention, the above-mentioned compound (A) corresponds to the compounds (a), and in the process-3 therein, the above-mentioned compound (B) corresponds to the compound (b).

The above-mentioned contacting is carried out with or without a solvent, preferably in an atmosphere of an inert gas, at usually −100 to 300° C., and preferably −80 to 200° C., for usually 1 minute to 200 hours, and preferably 10 minutes to 100 hours.

The above-mentioned solvent is generally inert to the compounds (A), (B), (C), (a) and (b), and the above-mentioned contact product. However, in the above-mentioned contacting methods (1), (2) and (3) consisting of two contacting steps, even a solvent active in the first contacting step (or the second contacting step) can be used in the second contacting step (or the first contacting step), so long as said solvent is inert in the second contacting step (or the first contacting step). Namely, a solvent used in the first contacting step may be different from a solvent used in the second contacting step.

Examples of the above-mentioned solvent are a non-polar solvent such as an aliphatic hydrocarbon solvent and an aromatic hydrocarbon solvent, and a polar solvent such as a halide solvent, an ether solvent, a carbonyl solvent, a phosphoric acid derivative, a nitrile solvent, a nitro compound, an amine solvent and a sulfur compound. Specific examples thereof are an aliphatic hydrocarbon solvent such as butane, pentane, hexane, heptane, octane, decane, 2,2,4-trimethylpentane and cyclohexane; an aromatic hydrocarbon solvent such as benzene, toluene and xylene; a halide solvent such as dichloromethane, difluoromethane, chloroform, 1,2-dichloroethane, 1,2-dibromoethane, 1,1,2-trichloro-1,2,2-trifluoroethane, tetrachloroethylene, chlorobenzene, bromobenzene and o-dichlorobenzene; an ether solvent such as dimethyl ether, diethyl ether, diisopropyl ether, di-n-butyl ether, methyl-tert-butyl ether, anisole, 1,4-dioxane, 1,2-dimethoxyethane, bis(2-methoxyethyl) ether, tetrahydrofuran and tetrahydropyran; a carbonyl solvent such as acetone, ethyl methyl ketone, cyclohexanone, acetic anhydride, ethyl acetate, butyl acetate, ethylene carbonate, propylene carbonate, N,N-dimethylformamide, N,N-dimethylacetamide and N-methyl-2-pyrrolidone; a phosphoric acid derivative such as hexamethylphosphate triamide and triethyl phosphate; a nitrile solvent such as acetonitrile, propionitrile, succinonitrile and benzonitrile; a nitro compound such as nitromethane and nitrobenzene; an amine solvent such as pyridine, piperidine and morpholine; and a sulfur compound such as dimethylsulfoxide and sulfolane.

In the process-1 of the present invention, the compound (B) is used in an amount of preferably 0.01 to 2.99, more preferably 0.10 to 2.80, further preferably 0.20 to 2.50, and most preferably 0.25 to 1.75, per 1 mol of the compound (A). Preferable, more preferable, further preferable and most preferable amounts of the compound (C) used per 1 mol of the compound (A) are calculated from the above-mentioned amounts of the compound (B) and the above formula (1), respectively. In the process-2 in accordance with the present invention, the above-mentioned compound (A) corresponds to the compounds (a), and in the process-3 therein, the above-mentioned compound (B) corresponds to the compound (b)

In order to promote further a reaction among the compounds of starting materials, it is preferable to add a step of heating at a higher temperature to the contacting step. An example of a method therefor is a method comprising the steps of (i) replacing a solvent contained in a reaction mixture produced in the contacting step with a solvent having a higher boiling point than that of the former solvent, hereby producing a mixture, and (ii) heating the mixture.

Also, in order to promote further a reaction among the compounds of starting materials, it is preferable to eliminate a by-product contained in a reaction mixture in the contacting step, or in the above-mentioned additional heating step, by an eliminating method according to properties of the by-product. Examples of the eliminating method are (i) a method comprising the step of eliminating a gaseous by-product through a gas-discharging apparatus installed in a reactor, and (ii) a method comprising the steps of evaporating a liquid by-product by heating a reaction mixture at a temperature higher than a boiling point of the liquid by-product, and then eliminating an evaporated gaseous by-product through a gas-discharging apparatus installed in a reactor.

The compound produced according to the processes of the present invention may contains the compounds (A), (B), (C), (a) or (b) of starting materials remaining unreacted, and the compound may be (i) a solution dissolved in a solvent used in said processes, (ii) a suspension suspended in a solvent used in said processes, or (iii) a solid produced by eliminating a solvent used in said processes.

It is preferable to add (i) a step of eliminating a solvent contained in a reaction mixture, and then (ii) a step of drying, to the contacting step of the processes of the present invention, or to the above-mentioned heating step. The drying step is carried out, for example, at 25° C. or higher for 0.5 to 24 hours under a reduced pressure.

The compound produced according to the processes of the present invention is useful to the above-mentioned catalyst component (A) for addition polymerization, especially for olefin polymerization.

From a viewpoint of producing a higher activity-carrying polymerization catalyst, the process for producing a catalyst for addition polymerization of the present invention preferably uses the component (C).

The component (B) used in the present invention is a transition metal compound capable of producing a single-site catalyst, and is not particularly limited as long as a combination thereof with the component (A) and the optional component (C) shows an addition polymerization activity. The term "single-site catalyst" in the present invention is a catalyst distinguished from a conventional solid catalyst. Said term means not only a narrow sense single-site catalyst capable of producing an addition polymer having (i) a narrow molecular weight distribution, and (ii) a high homogeneity, but also a catalyst capable of producing an addition polymer having (i) a broad molecular weight distribution, and (ii) a low homogeneity, which catalyst is produced by a process similar to a process for producing the narrow sense single-site catalyst.

The component (B) is preferably a transition metal compound of a transition metal of Groups 3 to 11 or the lanthanide series, and more preferably a transition metal compound represented by the following formula [6], or its μ-oxo type transition metal compound dimer,

   [6]

wherein $M^2$ is a transition metal atom of Groups 3 to 11 or the lanthanide series of the periodic table (IUPAC, 1989); $L^3$ is a cyclopentadiene-containing anionic group or a hetero atom-containing group, and when plural $L^3$s exist, they are the same as or different from one another, and are linked directly to one another or through a residual group containing a carbon atom, a silicon atom, a nitrogen atom, an oxygen atom, a sulfur atom or a phosphorus atom; $X^1$ is a halogen atom, a hydrocarbon group (excluding the above-mentioned cyclopentadiene-containing anionic group) or a hydrocarbyloxy group; a is a number satisfying $0<a \leq 8$; and b is a number satisfying $0<b \leq 8$. When $M^2$ is a titanium atom, a zirconium atom or a hafnium atom, both a and b are preferably 2. The above-mentioned "cyclopentadiene-containing anionic group" means a group having a cyclopentadienyl type anion skeleton.

Examples of $M^2$ in the formula [4] are a scandium atom, an yttrium atom, a titanium atom, a zirconium atom, a hafnium atom, a vanadium atom, a niobium atom, a tantalum atom, a chromium atom, an iron atom, a ruthenium atom, a cobalt atom, a rhodium atom, a nickel atom, a palladium atom, a samarium atom and an ytterbium atom. Among them, $M^2$ is preferably a titanium atom, a zirconium atom, a hafnium atom, a vanadium atom, a chromium atom, an iron atom, a cobalt atom or a nickel atom; particularly preferably a titanium atom, a zirconium atom or a hafnium atom; and most preferably a zirconium atom.

Examples of the above-mentioned cyclopentadiene-containing anionic group of $L^3$ are an $\eta^5$-(substituted)cyclopentadienyl group, an $\eta^5$-(substituted)indenyl group, and an $\eta^5$-(substituted)fluorenyl group; and groups obtained by substituting one or more hydrogen atoms contained in each of the above-mentioned cyclopentadiene-containing anionic groups with any of the hydrocarbon groups exemplified as of $L^1$ in the above formula [1]. Specific examples thereof are an $\eta^5$-cyclopentadienyl group, an $\eta^5$-methylcyclopentadienyl group, an $\eta^5$-ethylcyclopentadienyl group, an $\eta^5$-n-butylcyclopentadienyl group, an $\eta^5$-tert-butylcyclopentadienyl group, an $\eta^5$-1,2-dimethylcyclopentadienyl group, an $\eta^5$-1,3-dimethylcyclopentadienyl group, an $\eta^5$-1-methyl-2-ethylcyclopentadienyl group, an $\eta^5$-1-methyl-3-ethylcyclopentadienyl group, an $\eta^5$-1-tert-butyl-2-methylcyclopentadienyl group, an $\eta^5$-1-tert-butyl-3-methylcyclopentadienyl group, an $\eta^5$-1-methyl-2-isopropylcyclopentadienyl group, an $\eta^5$-1-methyl-3-isopropylcyclopentadienyl group, an $\eta^5$-1-methyl-2-n-butylcyclopentadienyl group, an $\eta^5$-1-methyl-3-n-butylcyclopentadienyl group, an $\eta^5$-1,2,3-trimethylcyclopentadienyl group, an $\eta^5$-1,2,4-trimethylcyclopentadienyl group, an $\eta^5$-tetramethylcyclopentadienyl group, an $\eta^5$-pentamethylcyclopentadienyl group, an $\eta^5$-indenyl group, an $\eta^5$-4,5,6,7-tetrahydroindenyl group, an $\eta^5$-2-methylindenyl group, an $\eta^5$-3-methylindenyl group, an $\eta^5$-4-methylindenyl group, an $\eta^5$-5-methylindenyl group, an $\eta^5$-6-methylindenyl group, an $\eta^5$-7-methylindenyl group, an $\eta^5$-2-tert-butylindenyl group, an $\eta^5$-3-tert-butylindenyl group, an $\eta^5$-4-tert-butylindenyl group, an $\eta^5$-5-tert-butylindenyl group, an $\eta^5$-6-tert-butylindenyl group, an $\eta^5$-7-tert-butylindenyl group, an $\eta^5$-2,3-dimethylindenyl group, an $\eta^5$-4,7-dimethylindenyl group, an $\eta^5$-2,4,7-trimethylindenyl an $\eta^5$-2-methyl-4-isopropylindenyl group, an $\eta^5$-4,5-benzindenyl group, an $\eta^5$-2-methyl-4,5-benzindenyl group, an $\eta^5$-4-phenylindenyl group, an $\eta^5$-2-methyl-5-phenylindenyl group, an $\eta^5$-2-methyl-4-phenylindenyl group, an $\eta^5$-2-methyl-4-naphthylindenyl group, an $\eta^5$-fluorenyl group, an $\eta^5$-2,7-dimethylfluorenyl group and an $\eta^5$-2,7-di-tert-butylfluorenyl group. The above term "$\eta^5$-" may be omitted hereinafter.

Examples of the hetero atom in the above-mentioned hetero atom-containing group of $L^3$ are an oxygen atom, a sulfur atom, a nitrogen atom and a phosphorus atom. The hetero atom-containing group is preferably an alkoxy group; an aryloxy group; a thioalkoxy group; a thioaryloxy group; an alkylamino group; an arylamino group; an alkylphosphino group; an arylphosphino group; a chelating ligand; an aromatic heterocyclic group containing, in its ring, one or more atoms selected from the group consisting of an oxygen atom, a sulfur atom, a nitrogen atom and a phosphorus atom; or an aliphatic heterocyclic group containing, in its ring, one or more atoms selected from the group consisting thereof.

Specific examples of the hetero atom-containing group are a methoxy group, an ethoxy group, a propoxy group, a butoxy group, a phenoxy group, a 2-methylphenoxy group, a 2,6-dimethylphenoxy group, a 2,4,6-trimethylphenoxy group, a 2-ethylphenoxy group, a 4-n-propylphenoxy group, a 2-isopropylphenoxy group, a 2,6-diisopropylphenoxy group, a 4-sec-butylphenoxy group, a 4-tert-butylphenoxy group, a 2,6-di-sec-butylphenoxy group, a 2-tert-butyl-4-methylphenoxy group, a 2,6-di-tert-butylphenoxy group, a 4-methoxyphenoxy group, a 2,6-dimethoxyphenoxy group, a 3,5-dimethoxyphenoxy group, a 2-chlorophenoxy group, a 4-nitrosophenoxy group, a 4-nitrophenoxy group, a 2-aminophenoxy group, a 3-aminophenoxy group, a 4-aminothiophenoxy group, a 2,3,6-trichlorophenoxy group, a 2,4,6-trifluorophenoxy group, a thiomethoxy group, a dimethylamino group, a diethylamino group, a dipropylamino group, a diphenylamino group, an isopropylamino group, a tert-butylamino group, a pyrrolyl group, a dimethylphosphino group, a 2-(2-oxy-1-propyl)phenoxy group, catechol, resorcinol, 4-isopropylcatechol, 3-methoxycatechol, a 1,8-dihydroxynahpthyl group, a 1,2-dihydroxynahpthyl group, a 2,2'-biphenyldiol group, a 1,1'-bi-2-naphthol group, a 2,2'-dihydroxy-6,6'-dimethylbiphenyl group, a 4,4',6,6'-tetra-tert-butyl-2,2'-methylenediphenoxy group, and a 4,4',6,6'-tetramethyl-2,2'-isobutylidenediphenoxy group.

A further example of the above-mentioned hetero atom-containing group is a group represented by the following formula [7],

   [7]

wherein three $R^4$s are independently of one another a hydrogen atom, a halogen atom or a hydrocarbon group; they are the same as, or different from one another; and two or more thereof may be linked to one another, in which they may form a ring.

Specific examples of $R^4$ in the above formula [7] are a fluorine atom, a chlorine atom, a bromine atom, an iodine atom, a methyl group, an ethyl group, a n-propyl group, an isopropyl group, a n-butyl group, a tert-butyl group, a cyclopropyl group, a cyclobutyl group, a cycloheptyl group, a cyclohexyl group, a phenyl group, a 1-naphthyl group, a 2-naphthyl group and a benzyl group.

A still further example of the above-mentioned hetero atom-containing group is a group represented by the following formula [8],

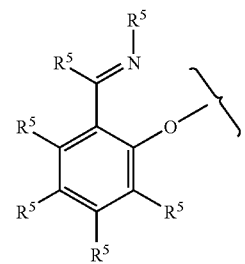

wherein six $R^5$s are independently of one another a hydrogen atom, a halogen atom, a hydrocarbon group, a halogenated hydrocarbon group, a hydrocarbyloxy group, a silyl group or an amino group; they are the same as, or different from one another; and two or more thereof may be linked to one another, in which they may form a ring.

Specific examples of $R^5$ in the formula [8] are a fluorine atom, a chlorine atom, a bromine atom, an iodine atom, a phenyl group, a 1-naphthyl group, a 2-naphthyl group, a tert-butyl group, a 2,6-dimethylphenyl group, a 2-fluorenyl group, a 2-methylphenyl group, a 4-trifluoropmethylphenyl group, a 4-methoxyphenyl group, a 4-pyridyl group, a cyclohexyl group, a 2-isopropylphenyl group, a benzyl group, a methyl group, a triethylsilyl group, a diphenylmethylsilyl group, a 1-methyl-1-phenylethyl group, a 1,1-dimethylpropyl group, a 2-chlorophenyl group and a pentafluorophenyl group.

The "chelating ligand" of $L^3$ in the above formula [6] means a ligand having two or more coordinating positions.

Specific examples thereof are acetylacetonate, diimine, oxazoline, bisoxazoline, terpyridine, acylhydrazone, diethylenetriamine, triethylenetetramine, porphyrin, crown ether and cryptate.

Specific examples of the heterocyclic group of $L^3$ in the above formula [6] are a pyridyl group, an N-substituted imidazolyl group and an N-substituted indazolyl group. Among them, preferred is a pyridyl group.

When plural $L^3$s in the above formula [6] are linked to one another through a residual group containing a carbon, silicon, nitrogen, oxygen, sulfur or phosphorus atom, namely, (1) when cyclopentadiene-containing anionic groups are linked to one another through the residual group, (2) when hetero atom-containing groups are linked to one another through the residual group, or (3) when the cyclopentadiene-containing anionic group and the hetero atom-containing group are linked to each other through the residual group, the residual group is preferably a two-valent residual group, wherein each of the two $L^3$s is linked to a carbon, silicon, nitrogen, oxygen, sulfur or phosphorus atom, and the number of atoms existing between the two $L^3$s is three or less, for example, in case of $L^3$-C(CH$_3$)$_2$—C(CH$_3$)$_2$-$L^3$, said number of atoms existing between the two $L^3$s is two.

Specific examples of the residual group are an alkylene group such as a methylene group, an ethylene group and a propylene group; a substituted alkylene group such as a dimethylmethylene group (an isopropylidene group) and a diphenylmethylene group; a silylene group; a substituted silylene group such as a dimethylsilylene group, a diethylsilylene group, a diphenylsilylene group, a tetramethyldisilylene group and a dimethoxysilylene group; and a hetero atom such as a nitrogen atom, an oxygen atom, a sulfur atom and a phosphorus atom. Among them, particularly preferred is a methylene group, an ethylene group, a dimethylmethylene group (an isopropylidene group), a diphenylmethylene group, a dimethylsilylene group, a diethylsilylene group, a diphenylsilylene group or a dimethoxysilylene group.

Examples of the halogen atom of $X^1$ in the above formula [6] are a fluorine atom, a chlorine atom, a bromine atom and an iodine atom. Examples of the hydrocarbon group of $X^1$ therein are an alkyl group, an aralkyl group, an aryl group and an alkenyl group. Among them, preferred is an alkyl group having 1 to 20 carbon atoms, an aralkyl group having 7 to 20 carbon atoms, an aryl group having 6 to 20 carbon atoms, or an alkenyl group having 3 to 20 carbon atoms.

Examples of said alkyl group having 1 to 20 carbon atoms are a methyl group, an ethyl group, a n-propyl group, an isopropyl group, a n-butyl group, a sec-butyl group, a tert-butyl group, an isobutyl group, a n-pentyl group, a neopentyl group, an amyl group, a n-hexyl group, a n-octyl group, a n-decyl group, a n-dodecyl group, a n-pentadecyl group and a n-eicosyl group. Among them, preferred is a methyl group, an ethyl group, an isopropyl group, a tert-butyl group, an isobutyl group or an amyl group.

One or more hydrogen atoms contained in the above-mentioned alkyl groups may be substituted with a halogen atom such as a fluorine atom, a chlorine atom, a bromine atom and an iodine atom. Examples of the alkyl group substituted with a halogen atom are a fluoromethyl group, a trifluoromethyl group, a chloromethyl group, a trichloromethyl group, a fluoroethyl group, a pentafluoroethyl group, a perfluoropropyl group, a perfluorobutyl group, a perfluorohexyl group, a perfluorooctyl group, a perchloropropyl group, a perchlorobutyl group and a perbromopropyl group.

Also, one or more hydrogen atoms contained in the above-mentioned alkyl groups may be substituted with an alkoxy group such as a methoxy group and an ethoxy group; an aryloxy group such as a phenoxy group; or an aralkyloxy group such as a benzyloxy group.

Examples of the above-mentioned aralkyl group having 7 to 20 carbon atoms are a benzyl group, a (2-methylphenyl) methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl)methyl group, a (3,5-dimethylphenyl)methyl group, a (2,3,4-trimethylphenyl)methyl group, a (2,3,5-trimethylphenyl)methyl group, a (2,3,6-trimethylphenyl)methyl group, a (3,4,5-trimethylphenyl)methyl group, a (2,4,6-trimethylphenyl)methyl group, a (2,3,4,5-tetramethylphenyl)methyl group, a (2,3,4,6-tetramethylphenyl)methyl group, a (2,3,5,6-tetramethylphenyl)methyl group, a (pentamethylphenyl) methyl group, an (ethylphenyl)methyl group, a (n-propylphenyl) methyl group, an (isopropylphenyl)methyl group, a (n-butylphenyl)methyl group, a (sec-butylphenyl) methyl group, a (tert-butylphenyl)methyl group, a(n-pentylphenyl)methyl group, a (neopentylphenyl)methyl group, a (n-hexylphenyl)methyl group, a (n-octylphenyl)methyl group, a (n-decylphenyl)methyl group, a (n-dodecylphenyl) methyl group, a naphthylmethyl group and an. anthracenylmethyl group. Among them, preferred is a benzyl group.

One or more hydrogen atoms contained in the above-mentioned aralkyl groups may be substituted with a halogen atom such as a fluorine atom, a chlorine atom, a bromine atom and an iodine atom; an alkoxy group such as a methoxy group and an ethoxy group; an aryloxy group such as a phenoxy group; or an aralkyloxy group such as a benzyloxy group.

Examples of the above-mentioned aryl group having 6 to 20 carbon atoms are a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, a n-propylphenyl group, an isopropylphenyl group, a n-butylphenyl group, a sec-butylphenyl group, a tert-butylphenyl group, a n-pentylphenyl group, a neopentylphenyl group, a n-hexylphenyl group, a n-octylphenyl group, a n-decylphenyl group, a n-dodecylphenyl group, a n-tetradecylphenyl group, a naphthyl group and an anthracenyl group. Among them, preferred is a phenyl group.

One or more hydrogen atoms contained in the above-mentioned aryl groups may be substituted with a halogen atom such as a fluorine atom, a chlorine atom, a bromine atom and an iodine atom; an alkoxy group such as a methoxy group and an ethoxy group; an aryloxy group such as a phenoxy group; or an aralkyloxy group such as a benzyloxy group.

Examples of the above-mentioned alkenyl group having 3 to 20 carbon atoms are an allyl group, a methallyl group, a crotyl group and a 1,3-diphenyl-2-propenyl group. Among them, preferred is an allyl group or a methallyl group.

Examples of the hydrocarbyloxy group of $X^1$ in the above formula [6] are an alkoxy group, an aralkyloxy group and an aryloxy group. Preferred is an alkoxy group having 1 to 20 carbon atoms, an aralkyloxy group having 7 to 20 carbon atoms or an aryloxy group having 6 to 20 carbon atoms.

Examples of said alkoxy group having 1 to 20 carbon atoms are a methoxy group, an ethoxy group, a n-propoxy group, an isopropoxy group, a n-butoxy group, a sec-butoxy group, a tert-butoxy group, a n-pentoxy group, a neopentoxy group, a n-hexoxy group, a n-octoxy group, a n-dodecoxy group, a n-pentadecoxy group and a n-eicosoxy group. Among them, preferred is a methoxy group, an ethoxy group, an isopropoxy group or a tert-butoxy group.

One or more hydrogen atoms contained in the above-mentioned alkoxy groups may be substituted with a halogen atom such as a fluorine atom, a chlorine atom, a bromine atom and an iodine atom; an alkoxy group such as a methoxy group and an ethoxy group; an aryloxy group such as a phenoxy group; or an aralkyloxy group such as a benzyloxy group.

Examples of the above-mentioned aralkyloxy group having 7 to 20 carbon atoms are a benzyloxy group, a (2-methylphenyl)methoxy group, a (3-methylphenyl)methoxy group, a (4-methylphenyl)methoxy group, a (2,3-dimethylphenyl)methoxy group, a (2,4-dimethylphenyl)methoxy group, a (2,5-dimethylphenyl)methoxy group, a (2,6-dimethylphenyl)methoxy group, a (3,4-dimethylphenyl)methoxy group, a (3,5-dimethylphenyl)methoxy group, a (2,3,4-trimethylphenyl)methoxy group, a (2,3,5-trimethylphenyl) methoxy group, a (2,3,6-trimethylphenyl)methoxy group, a (2,4,5-trimethylphenyl)methoxy group, a (2,4,6-trimethylphenyl)methoxy group, a (3,4,5-trimethylphenyl)methoxy group, a (2,3,4,5-tetramethylphenyl)methoxy group, a (2,3,4,6-tetramethylphenyl)methoxy group, a (2,3,5,6-tetramethylphenyl)methoxy group, a (pentamethylphenyl)methoxy group, an (ethylphenyl)methoxy group, a (n-propylphenyl)methoxy group, an (isopropylphenyl)methoxy group, a (n-butylphenyl)methoxy group, a (sec-butylphenyl)methoxy group, a (tert-butylphenyl)methoxy group, a (n-hexylphenyl)methoxy group, a (n-octylphenyl)methoxy group, a (n-decylphenyl)methoxy group, a naphthylmethoxy group and an anthracenylmethoxy group. Among them, preferred is a benzyloxy group.

One or more hydrogen atoms contained in the above-mentioned aralkyloxy groups may be substituted with a halogen atom such as a fluorine atom, a chlorine atom, a bromine atom and an iodine atom; an alkoxy group such as a methoxy group and an ethoxy group; an aryloxy group such as a phenoxy group; or an aralkyloxy group such as a benzyloxy group.

Examples of the above-mentioned aryloxy group having 6 to 20 carbon atoms are a phenoxy group, a 2-methylphenoxy group, a 3-methylphenoxy group, a 4-methylphenoxy group, a 2,3-dimethylphenoxy group, a 2,4-dimethylphenoxy group, a 2,5-dimethylphenoxy group, a 2,6-dimethylphenoxy group, a 3,4-dimethylphenoxy group, a 3,5-dimethylphenoxy group, a 2-tert-butyl-3-methylphenoxy group, a 2-tert-butyl-4-methylphenoxy group, a 2-tert-butyl-5-methylphenoxy group, a 2-tert-butyl-6-methylphenoxy group, a 2,3,4-trimethylphenoxy group, a 2,3,5-trimethylphenoxy group, a 2,3,6-trimethylphenoxy group, a 2,4,5-trimethylphenoxy group, a 2,4,6-trimethylphenoxy group, a 2-tert-butyl-3,4-dimethylphenoxy group, a 2-tert-butyl-3,5-dimethylphenoxy group, a 2-tert-butyl-3,6-dimethylphenoxy group, a 2,6-di-tert-butyl-3-methylphenoxy group, a 2-tert-butyl-4,5-dimethylphenoxy group, a 2,6-di-tert-butyl-4-methylphenoxy group, a 3,4,5-trimethylphenoxy group, a 2,3,4,5-tetramethylphenoxy group, a 2-tert-butyl-3,4,5-trimethylphenoxy group, a 2,3,4,6-tetramethylphenoxy group, a 2-tert-butyl-3,4,6-trimethylphenoxy group, a 2,6-di-tert-butyl-3,4-dimethylphenoxy group, a 2,3,5,6-tetramethylphenoxy group, a 2-tert-butyl-3,5,6-trimethylphenoxy group, a 2,6-di-tert-butyl-3,5-dimethylphenoxy group, a pentamethylphenoxy group, an ethylphenoxy group, a n-propylphenoxy group, an isopropylphenoxy group, a n-butylphenoxy group, a sec-butylphenoxy group, a tert-butylphenoxy group, a n-hexylphenoxy group, a n-octylphenoxy group, a n-decylphenoxy group, a n-tetradecylphenoxy group, a naphthoxy group and an anthracenoxy group.

One or more hydrogen atoms contained in the above-mentioned aryloxy groups may be substituted with a halogen atom such as a fluorine atom, a chlorine atom, a bromine atom and an iodine atom; an alkoxy group such as a methoxy group and an ethoxy group; an aryloxy group such as a phenoxy group; or an aralkyloxy group such as a benzyloxy group.

$X^1$ in the above formula [6] is more preferably a chlorine atom, a methyl group, an ethyl group, a n-propyl group, an isopropyl group, a n-butyl group, a methoxy group, an ethoxy group, a n-propoxy group, an isopropoxy group, a n-butoxy group, a trifluoromethoxy group, a phenyl group, a phenoxy group, a 2,6-di-tert-butylphenoxy group, a 3,4,5-trifluorophenoxy group, a pentafluorophenoxy group, a 2,3,5,6-tetrafluoro-4-pentafluorophenylphenoxy group or a benzyl group.

Examples of the transition metal compound represented by the above formula [6], wherein the transition metal atom is a titanium atom, a zirconium atom or a hafnium atom, are bis(cyclopentadienyl)titanium dichloride, bis(methylcyclopentadienyl)titanium dichloride, bis(ethylcyclopentadienyl) titanium dichloride, bis(n-butylcyclopentadienyl)titanium dichloride, bis(tert-butylcyclopentadienyl)titanium dichloride, bis(1,2-dimethylcyclopentadienyl)titanium dichloride, bis(1,3-dimethylcyclopentadienyl)titanium dichloride, bis (1-methyl-2-ethylcyclopentadienyl)titanium dichloride, bis (1-methyl-3-ethylcyclopentadienyl)titanium dichloride, bis (1-methyl-2-n-butylcyclopentadienyl)titanium dichloride, bis(1-methyl-3-n-butylcyclopentadienyl)titanium dichloride, bis(1-methyl-2-isopropylcyclopentadienyl)titanium dichloride, bis(1-methyl-3-isopropylcyclopentadienyl)titanium dichloride, bis(1-tert-butyl-2-methylcyclopentadienyl) titaniumdichloride, bis(1-tert-butyl-3-methylcyclopentadienyl)titaniumdichloride, bis(1,2,3-trimethylcyclopentadienyl)titanium dichloride, bis(1,2,4-trimethylcyclopentadienyl)titanium dichloride, bis (tetramethylcyclopentadienyl)titanium dichloride, bis (pentamethylcyclopentadienyl)titanium dichloride, bis (indenyl)titanium dichloride, bis(4,5,6,7-tetrahydroindenyl) titanium dichloride, bis(fluorenyl) titanium dichloride, bis (2-phenyindenyl)titanium dichloride, bis[2-(bis-3,5-trifluoromethylphenyl)indenyl]titanium dichloride, bis[2-(4-tert-butylphenyl)indenyl]titanium dichloride, bis[2-(4-trifluoromethylphenyl)indenyl]titanium dichloride, bis[2-(4-methyphenyl)indenyl]titanium dichloride, bis[2-(3,5-dimethylphenyl)indenyl]titanium dichloride, bis[2-(pentafluorophenyl)indenyl]titanium dichloride, cyclopentadienyl(pentamethylcyclopentadienyl) titanium dichloride, cyclopentadienyl(indenyl)titanium dichloride, cyclopentadienyl(fluorenyl)titanium dichloride, indenyl (fluorenyl)titanium dichloride, pentamethylcyclopentadienyl(indenyl)titanium dichloride, pentamethylcyclopentadienyl(fluorenyl)titanium dichloride, cyclopentadienyl(2-phenylindenyl)titanium dichloride, pentamethylcyclopentadienyl(2-phenylindenyl)titanium dichloride, dimethylsilylenebis(cyclopentadienyl)titanium dichloride, dimethylsilylenebis(2-methylcyclopentadienyl) titanium dichloride, dimethylsilylenebis (3-methylcyclopentadienyl) titanium dichloride, dimethylsilylenebis(2-n-butylcyclopentadienyl)titanium dichloride, dimethylsilylenebis(3-n-butylcyclopentadienyl) titanium dichloride, dimethylsilylenebis (2,3-dimethylcyclopentadienyl)titanium dichloride, dimethylsilylenebis(2,4-dimethylcyclopentadienyl) titanium dichloride, dimethylsilylenebis(2,5-dimethylcyclopentadienyl) titanium dichloride, dimethylsilylenebis(3,4-dimethylcyclopentadienyl) titanium dichloride, dimethylsilylenebis(2,3-ethylmethylcyclopentadienyl)titanium dichloride, dimethylsilylenebis(2,4-ethylmethylcyclopentadienyl)titanium dichloride, dimethylsilylenebis(2,5-ethylmethylcyclopentadienyl)titanium dichloride, dimethylsilylenebis(3,5-ethylmethylcyclopentadienyl)titanium dichloride, dimethylsilylenebis(2,3,4-trimethylcyclopentadienyl)titanium dichloride, dimethylsilylenebis(2,3,5-trimethylcyclopentadienyl)titanium dichloride, dimethylsilylenebis(tetramethylcyclopentadienyl)titanium dichloride, dimethylsilylenebis(indenyl)titanium dichloride, dimethylsilylenebis(2-methylindenyl)titanium dichloride, dimethylsilylenebis(2-tert-butylindenyl)titanium dichloride, dimethylsilylenebis(2,3-dimethylindenyl)titanium dichloride, dimethylsilylenebis(2,4,7-trimethylindenyl)titaniumdichloride, dimethylsilylenebis(2-methyl-4-isopropylindenyl)titanium dichloride, dimethylsilylenebis(4,5-benzindenyl)titanium dichloride, dimethylsilylenebis(2-methyl-4,5-benzindenyl) titanium dichloride, dimethylsilylenebis(2-phenylindenyl)titanium dichloride, dimethylsilylenebis(4-phenylindenyl)titanium dichloride, dimethylsilylenebis(2-methyl-4-phenylindenyl)titanium dichloride, dimethylsilylenebis(2-methyl-5-phenylindenyl) titanium dichloride, dimethylsilylenebis(2-methyl-4-naphthylindenyl)titanium dichloride, dimethylsilylenebis(4,5,6,7-tetrahydroindenyl) titanium dichloride, dimethylsilylene(cyclopentadienyl) (indenyl)titanium dichloride, dimethylsilylene(methylcyclopentadienyl)(indenyl)titanium dichloride, dimethylsilylene(n-butylcyclopentadienyl) (indenyl)titanium dichloride, dimethylsilylene(tetramethylcyclopentadienyl) (indenyl)titanium dichloride, dimethylsilylene (cyclopentadienyl)(fluorenyl)titanium dichloride, dimethylsilylene(methylcyclopentadienyl)(fluorenyl)titanium dichloride, dimethylsilylene(n-butylcyclopentadienyl) (fluorenyl)titanium dichloride, dimethylsilylene(tetramethylcyclopentadienyl) (indenyl)titanium dichloride, dimethylsilylene(indenyl)(fluorenyl)titanium dichloride, dimethylsilylenebis(fluorenyl)titanium dichloride, dimethylsilylene (cyclopentadienyl) (tetramethylcyclopentadienyl)titanium dichloride, dimethylsilylene(tetramethylcyclopentadienyl) (fluorenyl)titanium dichloride, cyclopentadienyltitanium trichloride, pentamethylcyclopentadienyltitanium trichloride, cyclopentadienyl(dimethylamido)titanium dichloride, cyclopentadienyl(phenoxy)titanium dichloride, cyclopentadienyl(2,6-dimethylphenyl)titanium dichloride, cyclopentadienyl(2,6-diisopropylphenyl)titanium dichloride, cyclopentadienyl(2,6-di-tert-butylphenyl)titanium dichloride, pentamethylcyclopentadienyl(2,6-dimethylphenyl)titanium dichloride, pentamethylcyclopentadienyl(2,6-diisopropylphenyl) titanium dichloride, pentamethylcyclopentadienyl (2,6-tert-butylphenyl)titanium dichloride, indenyl(2,6-diisopropylphenyl)titanium dichloride, fluorenyl(2,6-diisopropylphenyl)titanium dichloride, (tert-butylamido)tetramethylcyclopentadienyl-1,2-ethanediyl-titanium dichloride, (methylamido)tetramethylcyclopentadienyl-1,2-ethanediyl-titanium dichloride, (ethylamido)tetramethylcyclopentadienyl-1,2-ethanediyl-titanium dichloride, (tert-butylamido)tetramethylcyclopentadienyldimethylsilane titanium dichloride, (benzylamido)tetramethylcyclopentadienyldimethylsilane titanium dichloride, (phenylphosphido) tetramethylcyclopentadienyldimethylsilane titanium dichloride, (tert-butylamido)indenyl-1,2-ethanediyl titanium dichloride, (tert-butylamido)tetrahydroindenyl-1,2-ethanediyl titanium dichloride, (tert-butylamido)fluorenyl-1,2-ethanediyl titanium dichloride, (tert-butylamido)indenyldimethylsilane titanium dichloride, (tert-butylamido) tetrahydroindenyldimethylsilane titanium dichloride, (tert-butylamido)fluorenyldimethylsilane titanium dichloride, (dimethylaminomethyl)tetramethylcyclopentadienyl titanium(III) dichloride, (dimethylaminoethyl)tetramethylcyclopentadienyl titanium(III) dichloride, (dimethylaminopropyl)tetramethylcyclopentadienyl titanium(III) dichloride, (N-pyrrolidinylethyl)tetramethylcyclopentadienyl titanium dichloride, (B-dimethylaminoborabenzene)cyclopentadienyl titanium dichloride, cyclopentadienyl(9-mesitylboraanthracenyl)titanium dichloride, 2,2'-thiobis[4-methyl-6-tert-butylphenoxy]titanium dichloride, 2,2'-thiobis[4-methyl-6-(1-methylethyl) phenoxy]titanium dichloride, 2,2'-thiobis[4,6-dimethylphenoxy]titanium dichloride, 2,2'-thiobis(4-methyl-6-tert-butylphenoxy)titaniumdichloride, 2,2'-methylenebis(4-methyl-6-tert-butylphenoxy)titanium dichloride, 2,2'-ethylenebis(4-methyl-6-tert-butylphenoxy) titanium dichloride, 2,2'-sulfinylbis(4-methyl-6-tert-butylphenoxy)titanium dichloride, 2,2'-(4,4',6,6'-tetra-tert-butyl-1,1'-biphenoxy) titanium dichloride, (di-tert-butyl-1,3-propanediamido)titanium dichloride, (dicyclohexyl-1,3-propanediamido)titanium dichloride, [bis(trimethylsilyl)-1,3-propanediamido]titanium dichloride, [bis(tert-butyldimethylsilyl)-1,3-propanediamido]titanium dichloride, [bis(2,6-dimethylphenyl)-1,3-propanediamido] titanium dichloride, [bis(2,6-diisopropylphenyl)-1,3-propanediamido]titanium dichloride, [bis(2,6-di-tert-butylphenyl)-1,3-propanediamido]titanium dichloride, [bis(triisopropylsilyl) naphthalenediamido]titanium dichloride, [bis(trimethylsilyl)naphthalenediamido]titanium dichloride, [bis(tert-butyldimethylsilyl)naphthalenediamido]titanium dichloride, [hydrotris(3,5-dimethylpyrazolyl)borate]titanium trichloride, [hydrotris(3,5-diethylpyrazolyl)borate]titanium trichloride, [hydrotris(3,5-di-tert-butylpyrazolyl) borate]titanium trichloride, [tris(3,5-dimethylpyrazolyl)methyl]titanium trichloride, [tris(3,5-diethylpyrazolyl)methyl] titanium trichloride, [tris(3,5-di-tert-butylpyrazolyl)methyl] titanium trichloride, dimethylsilylene(cyclopentadienyl)(2-phenoxy)titanium dichloride, dimethylsilylene (cyclopentadienyl) (3-methyl-2-phenoxy)titanium dichloride, dimethylsilylene(cyclopentadienyl)(3,5-dimethyl-2-phenoxy) titanium dichloride, dimethylsilylene(cyclopentadienyl)(3-tert-butyl-2-phenoxy) titanium dichloride, dimethylsilylene(cyclopentadienyl)(3-tert-butyl-5-methyl-2-phenoxy)titanium dichloride, dimethylsilylene (cyclopentadienyl)(3,5-di-tert-butyl-2-phenoxy)titanium dichloride, dimethylsilylene(cyclopentadienyl)(5-methyl-3-phenyl-2-phenoxy)titanium dichloride, dimethylsilylene(cyclopentadienyl)(3-tert-butyldimethylsilyl-5-methyl-2-phenoxy)titanium dichloride, dimethylsilylene (cyclopentadienyl)(5-methyl-3-trimethylsilyl-2-phenoxy) titanium dichloride, dimethylsilylene(cyclopentadienyl)(3-tert-butyl-5-methoxy-2-phenoxy)titanium dichloride, dimethylsilylene(cyclopentadienyl)(3-tert-butyl-5-chloro-2-phenoxy)titanium dichloride, dimethylsilylene(cyclopentadienyl)(3,5-diamyl-2-phenoxy)titanium dichloride, dimethylsilylene(cyclopentadienyl)(3-phenyl-2-phenoxy)titanium dichloride and dimethylsilylene(cyclopentadienyl)(1-naphthoxy-2-yl)titanium dichloride; compounds formed by changing the term "titanium" contained in each of the above-mentioned compounds to the term "zirconium" or "hafnium"; compounds formed by changing the term "cyclopentadienyl" contained therein to the term "methylcyclopentadienyl", "n-butylcyclopentadienyl", "tert-butylcyclopentadienyl", "tetramethlycyclopentadienyl", "trimethylsilylcyclopentadienyl", "indenyl" or "fluorenyl";

compounds formed by changing the term "(2-phenoxy)" contained therein to the term "(3-phenyl-2-phenoxy)", "(3-trimethylsilyl-2-phenoxy)" or "(3-tert-butyldimethylsilyl-2-phenoxy)"; compounds formed by changing the term "dimethylsilylene" contained therein to the term "methylene", "ethylene", "dimethylmethylene (isopropylidene)", "diphenylmethylene", "diethylsilylene", "diphenylsilylene" or "dimethoxysilylene"; compounds formed by changing the term "dichloride" contained therein to the term "diethoxide", "di-n-propoxide", "diisopropoxide", "di-n-butoxide", "diisobutoxide", "di-tert-butoxide", "diphenoxide", "di(pentafluorophenoxide)" or "di(2,6-di-tert-butylphenoxide)"; and compounds formed by changing the term "trichloride" contained therein to the term "triethoxide", "tri-n-propoxide", "triisopropoxide", "tri-n-butoxide", "triisobutoxide", "tri-tert-butoxide", "triphenoxide", "tri(pentafluorophenoxide)" or "tri(2,6-di-tert-butylphenoxide)".

Examples of the transition metal compound represented by the above formula [6], wherein the transition metal atom is a nickel atom, are 2,2'-methylenebis[(4R)-4-phenyl-5,5'-dimethyloxazoline]nickel dichloride, 2,2'-methylenebis[(4R)-4-phenyl-5,5'-diethyloxazoline]nickel dichloride, 2,2'-methylenebis[(4R)-4-phenyl-5,5'-di-n-propyloxazoline]nickel dichloride, 2,2'-methylenebis[(4R)-4-phenyl-5,5'-diisopropyloxazoline]nickel dichloride, 2,2'-methylenebis[(4R)-4-phenyl-5,5'-dicyclohexyloxazoline]nickel dichloride, 2,2'-methylenebis[(4R)-4-phenyl-5,5'-dimethoxyoxazoline]nickel dichloride, 2,2'-methylenebis[(4R)-4-phenyl-5,5'-diethoxyoxazoline]nickel dichloride, 2,2'-methylenebis[(4R)-4-phenyl-5,5'-diphenyloxazoline]nickel dichloride, 2,2'-methylenebis[(4R)-4-phenyl-5,5'-di-(2-methylphenyl) oxazoline]nickel dichloride, 2,2'-methylenebis[(4R)-4-phenyl-5,5'-di-(3-methylphenyl) oxazoline]nickel dichloride, 2,2'-methylenebis[(4R)-4-phenyl-5,5'-di-(4-methylphenyl) oxazoline]nickel dichloride, 2,2'-methylenebis[(4R)-4-phenyl-5,5'-di-(2-methoxyphenyl) oxazoline]nickel dichloride, 2,2'-methylenebis[(4R)-4-phenyl-5,5'-di-(3-methoxyphenyl) oxazoline]nickel dichloride, 2,2'-methylenebis[(4R)-4-phenyl-5,5'-di-(4-methoxyphenyl) oxazoline]nickel dichloride, 2,2'-methylenebis[spiro{(4R)-4-phenyloxazoline-5,1'-cyclobutane}]nickel dichloride, 2,2'-methylenebis[spiro{(4R)-4-phenyloxazoline-5,1'-cyclopentane}]nickel dichloride, 2,2'-methylenebis[spiro{(4R)-4-phenyloxazoline-5,1'-cyclohexane}]nickel dichloride and 2,2'-methylenebis[spiro{(4R)-4-phenyloxazoline-5,1'-cycloheptane}]nickel dichloride; antipodes of the above-mentioned respective compounds; compounds formed by reversing a steric configuration of an asymmetric carbon on one oxazoline ring contained in each of the above-mentioned bisoxazoline compounds; compounds formed by changing the term "-4-phenyl" contained in each of the above-mentioned compounds to the term "-4-methyl", "-4-isopropyl", "-4-isobutyl", "-4-tert-butyl" or "-4-benzyl"; and compounds formed by changing the term "dichloride" contained therein to the term "diethoxide", "di-n-propoxide", "diisopropoxide", "di-n-butoxide", "diisobutoxide", "di-tert-butoxide", "diphenoxide", "di(pentafluorophenoxide)" or "di(2,6-di-tert-butyl- phenoxide)".

Further, examples of the compound represented by the above formula [6] are a nickel compound represented by the following formula; and a compound formed by changing the nickel atom contained in the following formula to a palladium atom, a cobalt atom, a rhodium atom or a ruthenium atom:

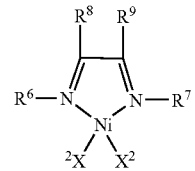

wherein each of $R^6$ and $R^7$ is a 2,6-diisopropylphenyl group; each of $R^8$ and $R^9$ is independently of each other a hydrogen atom, a methyl group or an acenaphthene group formed by incorporation of $R^8$ with $R^9$; and $X^2$ is a fluorine atom, a chlorine atom, a bromine atom, an iodine atom, a methyl group, an ethyl group, a n-propyl group, an isopropyl group, a n-butyl group, a phenyl group, a benzyl group, a methoxy group, an ethoxy group, or a phenoxy group.

Examples of the transition metal compound represented by the above formula [6], wherein the transition metal atom is an iron atom, are 2,6-bis-[1-(2,6-dimethylphenylimino) ethyl]pyridineiron dichloride, 2,6-bis-[1-(2,6-diisopropylphenylimino)ethyl]pyridineiron dichloride and 2,6-bis-[1-(2-tert-butyl-phenylimino)ethyl]pyridineiron dichloride; and compounds formed by changing the term "dichloride" contained in each of the above-mentioned compounds to the term "diethoxide", "di-n-propoxide", "diisopropoxide", "di-n-butoxide", "diisobutoxide", "di-tert-butoxide", "diphenoxide", "di(pentafluorophenoxide)" or "di(2,6-di-tert-butylphenoxide)".

Examples of the component (B) other than compounds represented by the above formula [6] are [hydrotris(3,5-dimethylpyrazolyl)borate]nickel chloride, [hydrotris(3,5-diethylpyrazolyl)borate]nickel chloride and [hydrotris(3,5-di-tert-butylpyrazolyl)borate]nickel chloride; compounds formed by changing the term "chloride" contained in each of the above-mentioned compounds to the term "ethoxide", "n-propoxide", "isopropoxide", "n-butoxide", "isobutoxide", "tert-butoxide", "phenoxide", "pentafluorophenoxide" or "2,6-di-tert-butylphenoxide": and compounds formed by changing the term "nickel" contained therein to the term "iron" or "cobalt".

Examples of a μ-oxo type transition metal compound of the transition metal compound represented by the above formula [6] are μ-oxobis[isopropylidene(cyclopentadienyl) (2-phenoxy)titanium chloride], μ-oxobis[isopropylidene(cyclopentadienyl) (3-tert-butyl-5-methyl-2-phenoxy)titanium chloride], μ-oxobis[isopropylidene(methylcyclopentadienyl) (2-phenoxy)titanium chloride], μ-oxobis[isopropylidene (methylcyclopentadienyl)(3-tert-butyl-5-methyl-2-phenoxy)titanium chloride], μ-oxobis[isopropylidene (tetramethylcyclopentadienyl) (2-phenoxy)titanium chloride], μ-oxobis[isopropylidene (tetramethylcyclopentadienyl)(3-tert-butyl-5-methyl-2-phenoxy)titanium chloride], μ-oxobis[dimethylsilylene(cyclopentadienyl) (2-phenoxy) titanium chloride], μ-oxobis[dimethylsilylene (cyclopentadienyl)(3-tert-butyl-5-methyl-2-phenoxy)titanium chloride], μ-oxobis[dimethylsilylene (methylcyclopentadienyl)(2-phenoxy)titanium chloride], μ-oxobis[dimethylsilylene(methylcyclopentadienyl) (3-tert-butyl-5-methyl-2-phenoxy)titanium chloride], μ-oxobis[dimethylsilylene (tetramethylcyclopentadienyl) (2-phenoxy)titanium chloride] and μ-oxobis[dimethylsilylene (tetramethylcyclopentadienyl)(3-tert-butyl-5-methyl-2-phenoxy)titanium chloride]; and compounds formed by changing the term "chloride" contained in each of the above-mentioned compounds to the term "ethoxide", "n-propoxide", "isopropoxide", "n-butoxide", "isobutoxide", "tert-butoxide", "phenoxide", "pentafluorophenoxide" or "2,6-di-tert-butylphenoxide".

The above-mentioned transition metal compounds are used singly, or in combination of two or more thereof.

Among the above-exemplified transition metal compounds as the component (B), preferred is the component (B) represented by the above formula [6]. Among them, preferred is the component (B) containing an atom of Group 4 as $M^2$ in the formula [6]; further preferred is the component (B) containing a cyclopentadiene-containing anionic group as at least one $L^3$ in the formula [6]; and particularly preferred is the component (B), wherein plural $L^3$s in the formula [6] are linked to one another through a residual group containing a carbon, silicon, nitrogen, oxygen, sulfur or phosphorus atom.

The component (C) may be an organoaluminum compound known in the art. Preferred is an organoaluminum compound represented by the following formula [9]:

$$R^{10}{}_c AlY_{3-c} \quad [9]$$

wherein $R^{10}$ is a hydrocarbon group, and when plural $R^{10}$s exist, they are the same as, or different from one another; Y is a hydrogen atom, a halogen atom, an alkoxy group, a aralkyloxy group or an aryloxy group, and when plural Ys exist, they are the same as, or different from one another; and c is a number satisfying $0 < c \leqq 3$.

$R^{10}$ in the above formula [9] is preferably a hydrocarbon group having 1 to 24 carbon atoms, and more preferably an alkyl group having 1 to 24 carbon atoms. Examples of $R^{10}$ are a methyl group, an ethyl group, a n-propyl group., a n-butyl group, an isobutyl group, a n-hexyl group, a 2-methylhexyl group and a n-octyl group. Among them, preferred is an ethyl group, a n-butyl group, an isobutyl group, a n-hexyl group, or a n-octyl group.

Examples of the halogen atom of Y in the above formula [9] are a fluorine atom, a chlorine atom, a bromine atom and an iodine atom, and preferred is a chlorine atom.

The alkoxy group of Y in the above formula [9] is preferably an alkoxy group having 1 to 24 carbon atoms. Examples thereof are a methoxy group, an ethoxy group, a n-propoxy group, an isopropoxy group, a n-butoxy group, a sec-butoxy group, a tert-butoxy group, a n-pentoxy group, a neopentoxy group, a n-hexoxy group, a n-octoxy group, a n-dodecoxy group, a n-pentadecoxy group and a n-eicoxy group. Among them, preferred is a methoxy group, an ethoxy group, or a tert-butoxy group.

The aralkyloxy group of Y in the above formula [9] is preferably an aralkyloxy group having 7 to 24 carbon atoms. Examples thereof are a benzyloxy group, a (2-methylphenyl)methoxy group, a (3-methylphenyl)methoxy group, a (4-methylphenyl)methoxy group, a (2,3-dimethylphenyl)methoxy group, a (2,4-dimethylphenyl)methoxy group, a (2,5-dimethylphenyl)methoxy group, a (2,6-dimethylphenyl)methoxy group, a (3,4-dimethylphenyl)methoxy group, a (3,5-dimethylphenyl)methoxy group, a (2,3,4-trimethylphenyl)methoxy group, a (2,3,5-trimethylphenyl)methoxy group, a (2,3,6-trimethylphenyl)methoxy group, a (2,4,5-trimethylphenyl)methoxy group, a (2,4,6-trimethylphenyl)methoxy group, a (3,4,5-trimethylphenyl)methoxy group, a (2,3,4,5-tetramethylphenyl)methoxy group, a (2,3,5,6-tetramethylphenyl)methoxy group, a (pentamethylphenyl)methoxy group, an (ethylphenyl)methoxy group, a (n-propylphenyl)methoxy group, an (isopropylphenyl)methoxy group, a (n-butylphenyl)methoxy group, a (sec-butylphenyl) methoxy group, a (tert-butylphenyl)methoxy group, a (n-hexylphenyl)methoxy group, a (n-octylphenyl)methoxy group, a (n-decylphenyl)methoxy group, a (n-tetradecylphenyl)methoxy group, a naphthylmethoxy group and an anthracenylmethoxy group. Among them, preferred is a benzyloxy group.

The aryloxy group of Y in the above formula [9] is preferably an aryloxy group having 6 to 24 carbon atoms. Examples thereof are a phenoxy group, a 2-methylphenoxy group, a 3-methylphenoxy group, a 4-methylphenoxy group, a 2,3-dimethylphenoxy group, a 2,4-dimethylphenoxy group, a 2,5-dimethylphenoxy group, a 2,6-dimethylphenoxy group, a 3,4-dimethylphenoxy group, a 3,5-dimethylphenoxy group, a 2,3,4-trimethylphenoxy group, a 2,3,5-trimethylphenoxy group, a 2,3,6-trimethylphenoxy group, a 2,4,5-trimethylphenoxy group, a 2,4,6-trimethylphenoxy group, a 3,4,5-trimethylphenoxy group, a 2,3,4,5-tetramethylphenoxy group, a 2,3,4,6-tetramethylphenoxy group, a 2,3,5,6-tetramethylphenoxy group, a pentamethylphenoxy group, an ethylphenoxy group, a n-propylphenoxy group, an isopropylphenoxy group, a n-butylphenoxy group, a sec-butylphenoxy group, a tert-butylphenoxy group, a n-hexylphenoxy group, a n-octylphenoxy group, a n-decylphenoxy group, a n-tetradecylphenoxy group, a naphtoxy group and an anthracenoxy group.

Examples of the organoaluminum compound represented by the above formula [9] are a trialkylaluminum such as trimethylaluminum, triethylaluminum, tri-n-propylaluminum, tri-n-butylaluminum, triisobutylaluminum, tri-n-hexylaluminum and tri-n-octylaluminum; a dialkylaluminum chloride such as dimethylaluminum chloride, diethylaluminum chloride, di-n-propylaluminum chloride, di-n-butylaluminum chloride, diisobutylaluminum chloride and di-n-hexylaluminum chloride; an alkylaluminum dichloride such as methylaluminum dichloride, ethylaluminum dichloride, n-propylaluminum dichloride, n-butylaluminum dichloride, isobutylaluminum dichloride and n-hexylaluminum dichloride; a dialkylaluminum hydride such as dimethylaluminum hydride, diethylaluminum hydride, di-n-propylaluminum hydride, di-n-butylaluminum hydride, diisobutylaluminum hydride and di-n-hexylaluminum hydride; an alkyl(dialkoxy)aluminum such as methy(dimethoxy)aluminum, methyl(diethoxy)aluminum and methyl(di-tert-butoxy)aluminum; a dialkyl(alkoxy)aluminum such as dimethy(methoxy)aluminum, dimethyl(ethoxy)aluminum and dimethyl(tert-butoxy)aluminum; an alkyl(diaryloxy)aluminum such as methyl(diphenoxy)aluminum, methylbis(2,6-diisopropylphenoxy)aluminum and methylbis(2,6-diphenylphenoxy)aluminum; and a dialkyl(aryloxy)aluminum such as dimethyl(phenoxy)aluminum, dimethyl(2,6-diisopropylphenoxy)aluminum and dimethyl(2,6-diphenylphenoxy)aluminum.

Among them, preferred is a trialkylaluminum; further preferred is trimethylaluminum, triethylaluminum, tri-n-butylaluminum, triisobutylaluminum, tri-n-hexylaluminum or tri-n-octylaluminum; and particularly preferred is triisobutylaluminum or tri-n-octylaluminum.

The above-mentioned organoaluminum compounds are used singly, or in combination of two or more thereof.

The component (B) is used in an amount of usually $1 \times 10^{-6}$ to $1 \times 10^{-3}$ mol, and preferably $5 \times 10^{-6}$ to $5 \times 10^{-4}$ mol per 1 g of the component (A).

The component (C) is used in an amount of preferably 0.01 to 10,000 mol, more preferably 0.1 to 5,000 mol, and most preferably 1 to 2,000 mol in terms of an amount of an aluminum atom contained in the component (C), per 1 mol of a transition metal atom contained in the component (B).

Examples of a method for contacting the component (A), the component (B) and an optional component (C) in the process for producing a catalyst for addition polymerization in accordance with the present invention are (1) a method comprising the steps of (i) contacting those components in a reactor for producing a catalyst, wherein a contacting order is not limited, and then (ii) feeding the catalyst to a polymerization reactor, (2) a method comprising the steps of (i) feeding those components separately to a polymerization reactor, and then (ii) contacting them in the polymerization reactor, and (3) a method comprising the steps of (i) contacting any two components of those components in a reactor for producing a catalyst, thereby producing a contact product, (ii) feeding the contact product and the remaining one component separately to a polymerization reactor, and then (iii) contacting them in the polymerization reactor.

Each of the components (A), (B) and (C) is used (1) in its solid state, (2) in its solution state obtained by dissolving the component in a hydrocarbon solvent completely free from an ingredient deactivating the component, such as water and oxygen, or (3) in its suspension state obtained by suspending the component in such a hydrocarbon solvent. Examples of the hydrocarbon solvent are an aliphatic hydrocarbon solvent such as butane, pentane, heptane, hexane and octane; an aromatic hydrocarbon solvent such as benzene and toluene; and a halogenated hydrocarbon such as methylene chloride. Among them, preferred is an aliphatic hydrocarbon or an aromatic hydrocarbon.

A concentration of the component (A) in the above-mentioned solution or suspension is usually 0.01 to 1000 g/liter, and preferably 0.1 to 500 g/liter; a concentration of the component (B) therein is usually 0.0001 to 1000 mmol/liter, and preferably 0.01 to 50 mmol/liter in terms of an amount of a transition metal atom contained in the component (B); and a concentration of the component (C) therein is usually 0.0001 to 100 mol/liter, and preferably 0.01 to 10 mol/liter in terms of an amount of an aluminum atom contained in the component (C).

A polymerization method in a process for producing an addition polymer in accordance with the present invention is not particularly limited. Examples of the polymerization method are (1) a gas-phase polymerization method comprising the step of polymerizing a gaseous addition polymerizable monomer, (2) a solution or slurry (suspension) polymerization method comprising the step of polymerizing an addition polymerizable monomer in a solvent, and (3) a bulk polymerization method comprising the step of polymerizing an addition polymerizable monomer using the addition polymerizable monomer as a solvent. Examples of the solvent used in the above-mentioned method (2) are an aliphatic hydrocarbon solvent such as butane, hexane, pentane, heptane and octane; an aromatic hydrocarbon solvent such as benzene and toluene; and a halogenated hydrocarbon solvent such as methylene chloride. Each of the above-mentioned polymerization methods is a batch-wise polymerization method or a continuous polymerization method, both of which may be carried out in two or more steps having different polymerization conditions from one another. A polymerization time is determined depending upon a kind of an addition polymer produced and a polymerization reactor, and it is generally 1 minute to 20 hours.

Examples of an addition polymerizable monomer in a process for producing an addition polymer in accordance with the present invention are an olefin, a diolefin, a cyclic olefin, an alkenyl aromatic hydrocarbon and a polar monomer. Those monomers are used singly or in combination of two or more thereof.

Specific examples of the above-mentioned monomers are an olefin such as ethylene, propylene, 1-butene, 1-pentene, 4-methyl-1-pentene, 5-methyl-1-hexene, 1-hexene, 1-heptene, 1-octene, 1-nonene, 1-decene and vinylcyclohexane; a diolefin such as 1,5-hexadiene, 1,4-hexadiene, 1,4-pentadiene, 1,7-octadiene, 1,8-nonadiene, 1,9-decadiene, 4-methyl-1,4-hexadiene, 5-methyl-1,4-hexadiene, 7-methyl-1,6-octadiene, 5-ethylidene-2-norbornene, dicyclopentadiene, 5-vinyl-2-norbornene, norbornadiene, 5-methylene-2-norbornene, 1,5-cyclooctadiene, 5,8-endomethylenehexahydronaphthalene, 1,3-butadiene, isoprene, 1,3-hexadinene, 1,3-octadiene, 1,3-cyclooctadiene and 1,3-cyclohexadiene; a cyclic olefin such as norbornene, 5-methyl-2-norbornene, 5-ethyl-2-norbornene, 5-butyl-2-norbornene, 5-phenyl-2-norbornene, 5-benzyl-2-norbornene, tetracyclododecene, tricyclodecene, tricycloundecene, pentacyclopentadecene, pentacyclohexadecene, 8-methyltetracyclododecene, 8-ethyltetracyclododecene, 5-acetyl-2-norbornene, 5-acetyloxy-2-norbornene, 5-methoxycarbonyl-2-norbornene, 5-ethoxycarbonyl-2-norbornene, 5-methyl-5-methoxycarbonyl-2-norbornene, 5-cyano-2-norbornene, 8-methoxycarbonyltetracyclododecene, 8-methyl-8-tetracyclododecene and 8-cyanotetracyclododecene; an alkenyl aromatic hydrocarbon such as styrene, an alkenylbenzene (for example, 2-phenylpropylene, 2-phenylbutene and 3-phenylpropylene), an alkylstyrene (for example, p-methylstyrene, m-methylstyrene, o-methylstyrene, p-ethylstyrene, m-ethylstyrene, o-ethylstyrene, α-methylstyrene, 2,4-dimethylstyrene, 2,5-dimethylstyrene, 3,4-dimethylstyrene, 3,5-dimethylstyrene, 3-methyl-5-ethylstyrene, 1,1-diphenylstyrene, p-tert-butylstyrene and p-sec-butylstyrene), a bis-alkenylbenzene (for example, divinylbenzene) and an alkenylnaphthalene (for example, 1-vinylnaphthalene); and a polar monomer such as an α,β-unsaturated carboxylic acid (for example, acrylic acid, methacrylic acid, fumaric acid, maleic anhydride, itaconic acid, itaconic anhydride and bicyclo(2,2,1)-5-heptene-2,3-dicarboxylic acid); a salt of the α,β-unsaturated carboxylic acid with a metal such as sodium, potassium, lithium, zinc, magnesium and calcium; an α,β-unsaturated carboxylic acid ester (for example, methyl acrylate, ethyl acrylate, n-propyl acrylate, isopropyl acrylate, tert-butyl acrylate, 2-ethylhexyl acrylate, methyl methacrylate, ethyl methacrylate, n-propyl methacrylate, isopropyl methacrylate, n-butyl methacrylate and isobutyl methacrylate); an unsaturated dicarboxylic acid (for example, maleic acid and itaconic acid); a vinyl ester (for example, vinyl acetate, vinyl propionate, vinyl caproate, vinyl caprate, vinyl laurate, vinyl stearate and vinyl trifluoroacetate); and an unsaturated carboxylic acid glycidyl ester (for example, glycidyl acrylate, glycidyl methacrylate and monoglycidyl itaconate).

An addition polymer produced according to a process of the present invention is a homopolymer or a copolymer. Examples of a combination of monomers in the copolymer are ethylene-propylene, ethylene-1-butene, ethylene-1-hexene, ethylene-1-octene, propylene-1-butene, ethylene-propylene-butene, and ethylene-propylene-1-hexene.

A catalyst for addition polymerization produced according to a process of the present invention is suitably used for producing an olefin polymer. Said olefin polymer is particularly preferably an ethylene-α-olefin copolymer. Among them, preferred is an ethylene-α-olefin copolymer having a polyethylene crystalline structure, wherein the α-olefin has preferably 3 to 8 carbon atoms such as 1-butene, 1-hexene and 1-octene.

EXAMPLE

The present invention is explained in more detail with reference to the following Examples, but the present invention is not limited thereto.

Example 1

(1) Production of Compound

Into a 200 ml four-necked flask purged with nitrogen, 90.0 ml of toluene and 10.0 ml (20.0 mmol of trimethylaluminum) of a toluene solution (concentration=2.00 mol/liter) of trimethylaluminum were put, and the resultant mixture was cooled to 5° C. To the cooled mixture, 2.8 ml (26.6 mmol) of 1,1,1,3,3,3-hexafluoro-2-propanol was added dropwise over 1.5 hours, and then, the mixture was stirred for 1.5 hours at 5° C. Thereafter, the mixture was heated to 40° C., and was stirred for 2 hours at 40° C. The mixture was allowed to stand overnight at a room temperature, and then, was cooled to 5° C. To this mixture, 0.35 ml (19.5 mmol) of water was added dropwise over 1 hour. Thereafter, the mixture was stirred at 5° C. for 1.5 hours, at 40° C. for 2 hours, and then, at 80° C. for 2 hours, in this order, thereby obtaining a deep green slurry of a compound. From an amount of trimethylaluminum used, a concentration of an aluminum atom contained in the slurry was calculated to be 0.2 mol/liter.

(2) Polymerization A 3 liter-volume autoclave equipped with a stirrer, which had been dried under a reduced pressure, and then purged with argon, was evacuated. Into the autoclave, 1000 ml of toluene and 30 g of 1-butene were fed, and then, the resultant mixture was heated to 70° C. Thereafter, ethylene was fed thereto so as to obtain its partial pressure of 0.6 MPa, and the system was stabilized. A gas chromatography analysis showed a gas composition in the system of 0% by mol of hydrogen, and 6.98% by mol of 1-butene. To the mixture, there was added 0.9 ml of a hexane solution (concentration=1 mmol/ml) of triisobutylaluminum. Next, 0.25 ml of a toluene solution (concentration=2 μmol/ml) of racemic ethylenebis(1-indenyl)zirconium diphenoxide, and 2.0 ml of the slurry produced in the above Example 1 (1) were added thereto, in this order. Polymerization was carried out at 70° C. for 40 minutes, during which an ethylene gas was fed thereto so as to keep the total pressure constant.

The obtained product was washed with a hydrochloric acid-methanol solution, and then, was dried under a reduced pressure, thereby obtaining 87 g of an olefin copolymer.

A polymerization activity per mol of a zirconium atom was $2.6 \times 10^8$ g/mol-Zr/hour. The obtained olefin copolymer had SCB (short chain branch number) of 23.2, and MFR (melt flow rate) of 2.1 g/10 minutes. Results are summarized in Table 1.

The above-mentioned "SCB" was measured by a method comprising the steps of:

(1) measuring an infrared absorption spectrum of the obtained olefin copolymer with an infrared spectrophotometer, FT-IR 7300, manufactured by Japan Spectroscopic Co., Ltd.;

(2) determining an amount of a 1-butene unit contained in the olefin copolymer from characteristic absorptions of an ethylene unit and a 1-butene unit in the infrared absorption spectrum, using a calibration curve prepared in advance; and (3) determining a short chain branch number (SCB) per 1000 carbon atoms in the olefin copolymer, from the amount of a 1-butene unit determined above.

The above-mentioned "MFR" was measured according to the method prescribed in Japanese Industrial Standards (JIS) K7210-1995 at 190° C. under a load of 21.18 N (2.16 kg), using a blend of the olefin copolymer with 1000 ppm of calcium stearate (antioxidant), and 1000 ppm of IRGANOX 1076 (antioxidant). Generally, the smaller the MFR is, the higher a molecular weight of the olefin copolymer is.

Example 2

(1) Production of Compound

Example 1 (1) was repeated except that (i) the amount of toluene was changed to 97.0 ml, and (ii) 10.0 ml (20.0 mmol of trimethylaluminum) of a toluene solution (concentration=2.00 mol/liter) of trimethylaluminum was changed to 2.7 ml (20 mmol) of triethylaluminum, thereby obtaining a slurry of a compound.

(2) Polymerization

Example 1 (2) was repeated except that (i) the slurry produced in Example 1 (1) was changed to 2.0 ml of the slurry produced in the above Example 2 (1), and (ii) the gas chromatography analysis showed a gas composition in the system of 0% by mol of hydrogen, and 6.71% by mol of 1-butene, thereby obtaining 86 g of an olefin copolymer.

A polymerization activity per mol of a zirconium atom was $2.6 \times 10^8$ g/mol-Zr/hour. The obtained olefin copolymer had SCB of 23.5, and MFR of 2.4 g/10 minutes. Results are summarized in Table 1.

Comparative Example 1

(1) Polymerization

Example 1 (2) was repeated except that (i) the slurry produced in Example 1 (1) was changed to 2.0 ml of a toluene solution (concentration=0.2 mol/ml) of polymethylaluminoxane having a tradename of PMAO, manufactured by Tosoh-finechem, and (ii) the gas chromatography analysis showed a gas composition in the system of 0% by mol of hydrogen, and 8.18% by mol of 1-butene, thereby obtaining 39 g of an olefin copolymer.

A polymerization activity per mol of a zirconium atom was $1.2 \times 10^8$ g/mol-Zr/hour. The obtained olefin copolymer had SCB of 16.1, and MFR of 5.6 g/10 minutes. Results are summarized in Table 1.

Comparative Example 2

(1) Production of Compound

Example 1 (1) was repeated except that the step of "adding 1,1,1,3,3,3-hexafluoro-2-propanol" to the step of "cooling the mixture to 5° C." were omitted, thereby obtaining a pale white slurry of a compound. From an amount of trimethylaluminum used, a concentration of an aluminum atom contained in the slurry was calculated to be 0.2 mol/liter.

(2) Polymerization

Example 1 (2) was repeated except that (i) the slurry produced in Example 1 (1) was changed to 2.0 ml of the slurry obtained in the above Comparative Example 2 (1), and (ii) the gas chromatography analysis showed a gas composition in the system of 0% by mol of hydrogen, and 7.31% by mol of 1-butene, thereby obtaining 53 g of an olefin copolymer.

A polymerization activity per mol of a zirconium atom was $1.6 \times 10^8$ g/mol-Zr/hour. The obtained olefin copolymer had SCB of 15.7, and MFR of 4.8 g/10 minutes. Results are summarized in Table 1.

Reference Example 1

(1) Production of Compound

Example 1 (1) was repeated except that (i) the amount of toluene was changed to 97.0 ml, (ii) 10.0 ml (20.0 mmol) of a toluene solution (concentration=2.00 mol/liter) of trimethylaluminum was changed to 2.7 ml (20 mmol) of triethylaluminum, and (iii) the step of "adding 1,1,1,3,3,3-hexafluoro-2-propanol" to the step of "cooling the mixture to 5° C." were omitted, thereby obtaining a slurry of a compound.

(2) Polymerization

Example 1 (2) was repeated except that (i) the slurry produced in Example 1 (1) was changed to 2.0 ml of the slurry obtained in the above Reference Example 1 (1), and (ii) the gas chromatography analysis showed a gas composition in the system of 0% by mol of hydrogen, and 8.20% by mol of 1-butene, thereby obtaining 26 g of an olefin copolymer.

A polymerization activity per mol of a zirconium atom was $8.1 \times 10^7$ g/mol-Zr/hour. The obtained olefin copolymer had SCB of 14.8, and MFR of 5.0 g/10 minutes. Results are summarized in Table 1.

TABLE 1

|  | Example | | Comparative Example | | Reference |
| --- | --- | --- | --- | --- | --- |
|  | 1 | 2 | 1 | 2 | Example 1 |
| Compound (A) (Note 1) | TMA | TEA | PMAO | TMA | TEA |
| Compound (B) (Note 2) | HFP | HFP | — | — | — |
| Compound (C) | water | water |  | water | water |
| Concentration of 1-butene (% by mol) | 6.98 | 6.71 | 8.18 | 7.31 | 8.20 |
| Polymerization Activity (g/mol-Zr/hour) | $2.6 \times 10^8$ | $2.6 \times 10^8$ | $1.2 \times 10^8$ | $1.6 \times 10^8$ | $8.1 \times 10^7$ |
| Olefin copolymer |  |  |  |  |  |
| SCB | 23.2 | 23.5 | 16.1 | 15.7 | 14.8 |
| MFR (g/10 min.) | 2.1 | 2.4 | 5.6 | 4.8 | 5.0 |

(Note 1)
TMA: trimethylaluminum
TEA: triethylaluminum
(Note 2)
HFP: 1,1,1,3,3,3-hexafluoro-2-propanol

The invention claimed is:

1. A process for producing a compound, which comprises the step of contacting a compound (A) represented by the following formula [1], a compound (B) represented by the following formula [2], and a compound (C) represented by the following formula [3] with one another:

$$M^1 L^1_3 \qquad [1],$$

$$R^1_{t-1} TH \qquad [2] \text{ and}$$

$$R^2_{t-2} TH_2 \qquad [3],$$

in respective molar amounts satisfying the following formula (1), $$3 \times (\text{molar amount of the compound (A)}) \leq (\text{molar amount of the compound (B)}) + 2 \times (\text{molar amount of the compound (C)}) \qquad (1),$$

wherein $M^1$ is an atom of Group 13 in the periodic table; $L^1$ is a hydrogen atom, a hydrocarbon group or a halogen atom, three $L^1$s are the same as or different from one another, and at least one $L^1$ is a hydrocarbon group; $R^1$ is an electron-withdrawing group or a group containing an electron-withdrawing group, and when plural $R^1$s exist, they are the same as or different from one another; $R^2$ is a hydrocarbon group or a halogenated hydrocarbon group; T is independently of each other a non-metal atom of Group 15 or 16 in the periodic table; and t is the valence of T.

2. A catalyst component for addition polymerization, which comprises a compound produced by the process according to claim 1.

3. A process for producing a catalyst for addition polymerization, which comprises the step of contacting the catalyst component (A) according to claim 2 with a transition metal compound (B) and an optional organoaluminum compound (C).

4. The process for producing a catalyst for addition polymerization according to claim 3, wherein the transition metal compound (B) has at least one cyclopentadiene-containing anionic group.

5. A process for producing an addition polymer, which comprises the step of addition polymerizing an addition polymerizable monomer in the presence of a catalyst for addition polymerization produced by the process according to claim 3.

6. The process for producing an addition polymer according to claim 5, wherein the addition polymerizable monomer is an olefin.

7. The process for producing an addition polymer according to claim 5, wherein the addition polymerizable monomer is a combination of ethylene with an α-olefin.

8. A process for producing a compound, which comprises the step of contacting a compound (a) represented by the following formula [4], a compound (B) represented by the following formula [2], and a compound (C) represented by the following formula [3] with one another:

$$\text{EtAlL}^2_2 \qquad [4],$$

$$R^1_{t-1} TH \qquad [2] \text{ and}$$

$$R^2_{t-2} TH_2 \qquad [3],$$

wherein $L^2$ is a hydrogen atom, a hydrocarbon group having two or more carbon atoms, or a halogen atom, and two $L^1$s are the same as or different from each another; $R^1$ is an electron-withdrawing group or a group containing an electron-withdrawing group, and when plural $R^1$s exist, they are the same as or different from one another; $R^2$ is a hydrocarbon group or a halogenated hydrocarbon group; T is independently of each other a non-metal atom of Group 15 or 16 in the periodic table; and t is the valence of T.

9. The process for producing a compound according to claim 8, wherein the compound (a) is triethylaluminum.

10. A catalyst component for addition polymerization, which comprises a compound produced by the process according to claim 8.

11. A process for producing a catalyst for addition polymerization, which comprises the step of contacting the catalyst component (A) according to claim 10 with a transition metal compound (B) and an optional organoaluminum compound (C).

12. The process for producing a catalyst for addition polymerization according to claim 11, wherein the transition metal compound (B) has at least one cyclopentadiene-containing anionic group.

13. A process for producing an addition polymer, which comprises the step of addition polymerizing an addition polymerizable monomer in the presence of a catalyst for addition polymerization produced by the process according to claim 11.

14. The process for producing an addition polymer according to claim 13, wherein the addition polymerizable monomer is an olefin.

15. The process for producing an addition polymer according to claim 13, wherein the addition polymerizable monomer is a combination of ethylene with an α-olefin.

16. A process for producing a compound, which comprises the step of contacting a compound (A) represented by the following formula [1], a compound (b) represented by the following formula [5], and a compound (C) represented by the following formula [3] with one another:

$$M^1L^1_3 \qquad [1],$$

$$R^3OH \qquad [5], \text{ and}$$

$$R^{2t-2}TH_2 \qquad [3],$$

wherein $M^1$ is an atom of Group 13 in the periodic table; $L^1$ is a hydrogen atom, a hydrocarbon group or a halogen atom, three $L^1$s are the same as or different from one another, and at least one $L^1$ is a hydrocarbon group; $R^3$ is a halogenated alkyl group; $R^2$ is a hydrocarbon group or a halogenated hydrocarbon group; T is independently of each other a non-metal atom of Group 15 or 16 in the periodic table; and t is the valence of T.

17. A catalyst component for addition polymerization, which comprises a compound produced by the process according to claim 16.

18. A process for producing a catalyst for addition polymerization, which comprises the step of contacting the catalyst component (A) according to claim 17 with a transition metal compound (B) and an optional organoaluminum compound (C).

19. The process for producing a catalyst for addition polymerization according to claim 18, wherein the transition metal compound (B) has at least one cyclopentadiene-containing anionic group.

20. A process for producing an addition polymer, which comprises the step of addition polymerizing an addition polymerizable monomer in the presence of a catalyst for addition polymerization produced by the process according to claim 18.

21. The process for producing an addition polymer according to claim 20, wherein the addition polymerizable monomer is an olefin.

22. The process for producing an addition polymer according to claim 20, wherein the addition polymerizable monomer is a combination of ethylene with an α-olefin.

* * * * *